United States Patent
Murray et al.

(10) Patent No.: US 11,650,198 B2
(45) Date of Patent: *May 16, 2023

(54) PLASMA SEPARATION DEVICE

(71) Applicant: ViveBio Scientific, LLC, Alpharetta, GA (US)

(72) Inventors: Timothy Murray, Alpharetta, GA (US); Daniel Braun, Carlsbad, CA (US); Brian Weinberg, Carlsbad, CA (US)

(73) Assignee: VIVEBIO SCIENTIFIC, LLC, Alpharetta, GA (US)

( * ) Notice: Subject to any disclaimer, the term of this patent is extended or adjusted under 35 U.S.C. 154(b) by 234 days.

This patent is subject to a terminal disclaimer.

(21) Appl. No.: 16/884,535

(22) Filed: May 27, 2020

(65) Prior Publication Data

US 2021/0018487 A1    Jan. 21, 2021

Related U.S. Application Data

(63) Continuation of application No. 16/515,439, filed on Jul. 18, 2019, now Pat. No. 10,690,654, which is a
(Continued)

(51) Int. Cl.
*G01N 33/49* (2006.01)
*B01D 53/22* (2006.01)
(Continued)

(52) U.S. Cl.
CPC ......... *G01N 33/491* (2013.01); *B01D 53/228* (2013.01); *B01D 63/08* (2013.01);
(Continued)

(58) Field of Classification Search
CPC ............ G01N 33/491; A61B 5/150755; B01D 53/228; B01D 63/08; B01D 63/082;
(Continued)

(56) References Cited

U.S. PATENT DOCUMENTS 3,872,576 A    3/1975  Mott
4,449,539 A    5/1984  Sarstedt
(Continued)

FOREIGN PATENT DOCUMENTS

WO    2016/019113 A1    2/2016
WO    2016/025726 A1    2/2016
WO    2019/140950 A1    8/2018

OTHER PUBLICATIONS

European Extended Search Report and for EP Application No. 18744005.2 dated Oct. 14, 2020 (6 pages).
(Continued)

*Primary Examiner* — John Kim
(74) *Attorney, Agent, or Firm* — Eversheds Sutherland (US) LLP

(57) ABSTRACT

Devices and methods are provided that permit efficient and selective separation of liquid biological specimens into at least two constituent components to facilitate subsequent quantitative and qualitative analysis on at least one analyte of interest in at least one of the components. The devices generally include one or more sample deposition regions supported on a base. Each sample deposition region includes a separation membrane for separating the liquid biological specimen into two different fractions. The first fraction is trapped by the separation membrane while the second fraction passes through the separation membrane and into a respective collection membrane. The separation and collection membranes are easily separable from the devices and can be utilized for further processing and analysis.

19 Claims, 16 Drawing Sheets

Related U.S. Application Data continuation of application No. PCT/US2018/015969, filed on Jan. 30, 2018.

(60) Provisional application No. 62/451,945, filed on Jan. 30, 2017.

(51) Int. Cl.

| | |
|---|---|
| *B01D 63/08* | (2006.01) |
| *B01D 69/02* | (2006.01) |
| *B01D 69/06* | (2006.01) |
| *B01D 69/10* | (2006.01) |
| *B01D 69/12* | (2006.01) |
| *B01D 71/04* | (2006.01) |
| *B01D 71/06* | (2006.01) |
| *B01D 71/26* | (2006.01) |
| *B01D 71/68* | (2006.01) |
| *A61B 5/15* | (2006.01) |

(52) U.S. Cl.
CPC ......... *B01D 63/082* (2013.01); *B01D 63/087* (2013.01); *B01D 63/088* (2013.01); *B01D 69/02* (2013.01); *B01D 69/06* (2013.01); *B01D 69/10* (2013.01); *B01D 69/12* (2013.01); *B01D 71/04* (2013.01); *B01D 71/06* (2013.01); *B01D 71/26* (2013.01); *B01D 71/68* (2013.01); *A61B 5/150755* (2013.01); *B01D 2201/04* (2013.01); *B01D 2201/18* (2013.01); *B01D 2201/301* (2013.01); *B01D 2201/305* (2013.01); *B01D 2201/306* (2013.01); *B01D 2201/307* (2013.01); *B01D 2201/52* (2013.01); *B01D 2239/0471* (2013.01); *B01D 2239/0492* (2013.01); *B01D 2239/1208* (2013.01); *B01D 2239/1216* (2013.01); *B01D 2313/02* (2013.01); *B01D 2313/025* (2013.01); *B01D 2325/02* (2013.01); *B01D 2325/022* (2013.01); *B01L 2300/021* (2013.01); *B01L 2300/04* (2013.01); *B01L 2300/041* (2013.01); *B01L 2300/042* (2013.01); *B01L 2300/043* (2013.01); *B01L 2300/0681* (2013.01); *B01L 2400/0406* (2013.01); *B01L 2400/0457* (2013.01)

(58) Field of Classification Search
CPC .... B01D 63/087; B01D 63/088; B01D 69/02; B01D 69/06; B01D 69/10; B01D 69/12; B01D 69/148; B01D 71/04; B01D 71/06; B01D 71/26; B01D 71/68; B01D 2201/04; B01D 2201/18; B01D 2201/301; B01D 2201/305; B01D 2201/306; B01D 2201/307; B01D 2201/52; B01D 2239/0471; B01D 2239/0492; B01D 2239/1208; B01D 2239/1216; B01D 2313/02; B01D 2313/025; B01D 2325/02; B01D 2325/022; B01L 2300/021; B01L 2300/04; B01L 2300/041; B01L 2300/042; B01L 2300/043; B01L 2300/0681; B01L 2400/0406; B01L 2400/0457
See application file for complete search history.

(56) References Cited

U.S. PATENT DOCUMENTS

| | | |
|---|---|---|
| 4,933,092 A | 6/1990 | Aunet et al. |
| 5,240,862 A | 8/1993 | Koenhen et al. |
| 5,361,920 A | 11/1994 | Nozawa et al. |
| 2004/0060859 A1 | 4/2004 | Seshimoto et al. |
| 2006/0188392 A1 | 8/2006 | Tanaka et al. |
| 2012/0305500 A1 | 12/2012 | Bormann et al. |
| 2013/0323711 A1 | 12/2013 | Singh et al. |

OTHER PUBLICATIONS

PCT International Search Report and Written Opinion for PCT/US2018/015969 dated Mar. 22, 2018 (9 pages).

PLASMA SEPARATION DEVICE

CROSS REFERENCE TO RELATED APPLICATION

This application is a continuation of U.S. application Ser. No. 16/515,439, filed Jul. 18, 2019, now U.S. Pat. No. 10,690,654, which is a continuation of PCT Application No. PCT/US2018/015969, filed Jan. 30, 2018, which claims the benefit of U.S. Provisional Patent Application No. 62/451,945, filed on Jan. 30, 2017. The entire contents of which are incorporated by reference herewith.

FIELD OF INVENTION

The present disclosure generally relates to devices and methods that permit efficient and selective separation of liquid biological specimens (e.g. biological fluids or biological specimen containing suspensions) into at least two constituent components to facilitate subsequent quantitative and qualitative analysis on at least one analyte of interest in at least one of the components.

BACKGROUND OF THE INVENTION

Biological specimens are often collected for analysis of the levels and concentrations of various analytes contained therein. Although many diagnostics are carried out on biological specimens in their native state, many times the biological specimen must be separated into its constituent components for a variety of reasons. Separating a biological specimen into different constituent parts can maximize the precision, accuracy, and reproducibility of detecting and quantifying analytes of interest within the biological specimen. For example, it is often necessary to filter out solid components from whole blood (e.g., white blood cells, red blood cells, etc.), separate blood serum from whole blood, and separate blood plasma from whole blood, to improve not only the recovery of select analytes from the biological specimen (e.g. viruses, plasma proteins, cytokines, chemokines, immunglobins, etc.) but also improve the subsequent detection and analysis of those analytes. As one example, red blood cells (erythrocytes) scatter and absorb light and, therefore, can adversely affect diagnostic tests that rely on measurements of either reflected or transmitted light. Removing red blood cells can help obtain the most accurate reading possible.

Traditionally, liquid biological specimens have been separated by centrifugation. For example, blood plasma and serum have been separated from whole blood by centrifuging either before (for plasma) or after (for serum) clotting. However, centrifugation requires electricity and expensive equipment that may not be readily available in a clinical laboratory or out in the field. Further, centrifugation can damage analytes of interest (e.g. nucleic acids such as DNA and RNA).

A number of techniques have been devised to avoid this problem. The techniques generally utilize a filtering device that separates a liquid biological specimen into various components. However, these devices have proven to be unsuitable for a variety of reasons. Therefore, what are needed are improved devices and methods that permit efficient and selective separation of liquid biological specimens into at least two constituent components to facilitate subsequent quantitative and qualitative analysis on at least one analyte of interest in at least one of the components.

SUMMARY OF THE INVENTION

This disclosure generally provides liquid biological specimen separation devices and methods of using the same. In some aspects, a liquid biological specimen separation device is provided that comprises a base; a collection membrane disposed on the base, a separation membrane disposed on the collection membrane; and a cover disposed on the separation membrane, wherein the cover comprises an aperture therein configured to allow deposition of a liquid biological specimen. In other aspects, a liquid biological specimen separation device is provided that comprises a base; a plurality of collection membranes disposed on the base; a plurality of separation membranes, wherein each separation membrane is disposed on a corresponding one of the collection membranes; and a plurality of covers, wherein each cover is disposed on a corresponding one of the separation membranes, and wherein each cover comprises an aperture therein configured to allow deposition of a liquid biological specimen therethrough. In other aspects, a liquid biological specimen separation device is provided that comprises a base; a collection membrane disposed in the base, a separation membrane disposed in the base and on the collection membrane, and a cap disposed on the separation membrane and base, wherein the cap comprises an aperture therein configured to allow deposition of a liquid biological specimen.

BRIEF DESCRIPTION OF THE DRAWINGS

Referring now to the drawings, which are meant to be exemplary and not limiting, and wherein like elements are numbered alike. The detailed description is set forth with reference to the accompanying drawings illustrating examples of the disclosure, in which use of the same reference numerals indicates similar or identical items. Certain embodiments of the present disclosure may include elements, components, and/or configurations other than those illustrated in the drawings, and some of the elements, components, and/or configurations illustrated in the drawings may not be present in certain embodiments.

DETAILED DESCRIPTION OF THE INVENTION

Figure 1A:
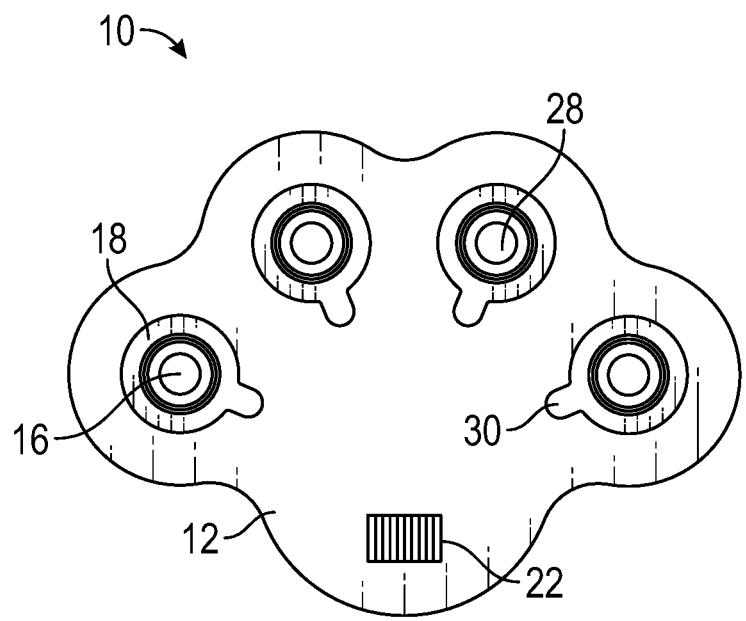
FIGS. 1A-1B show a liquid specimen separation device in accordance with one example embodiment of the disclosure.

Devices and methods are provided that permit efficient and selective separation of liquid biological specimens into at least two constituent components to facilitate subsequent quantitative and qualitative analysis on at least one analyte of interest in at least one of the components. The devices and methods fulfill the need for a convenient and simple method for filtering, separating, and/or storing an analyte of interest.

Examples of biological specimen suitable for use with devices described herein include whole blood, plasma, urine, saliva, sputum, semen, vaginal lavage, bone marrow, breast milk, and cerebrospinal fluid. One advantage of the present devices is that they can sufficiently preserve analytes of interest.

The devices generally include one or more sample deposition regions supported on an ergonomically configured base that permits ease of handling. Each sample deposition region includes a separation membrane for separating the liquid biological specimen into two different fractions. The first fraction is trapped by the separation membrane while the second fraction passes through the separation membrane and into a respective collection membrane. The separation and collection membranes are easily separable from the devices and can be utilized for further processing and analysis. The devices can include other features such as one or more covers (e.g. stickers) or caps that define the sample deposition regions, secure the separation membranes, collection membranes, and/or base together or in place, urge the separation membranes, collection membranes, and/or base together, and allows for easy removal of the separation and/or collection membranes from the device. The devices can also include identification markers (e.g. barcodes) on the base.

The devices can be used to trap and filter out solid components from a liquid biological specimen. For example, the devices can include a separation membrane that filters and traps solid components of a whole blood specimen (e.g. red blood cells, white blood cells, erythrocytes), thereby resulting in the collection membrane absorbing cell-free serum, plasma, and plasma proteins.

As used herein, the term "analyte" refers to any micro- or macro-molecules in a biological specimen that are to be detected or analyzed. These include, for example, nucleic acids (e.g. DNA, RNA), polynucleotides, oligonucleotides, proteins, polypeptides, oligopeptides, enzymes, amino acids, receptors, carbohydrates, lipids, whole cells, cellular fragments, any intra- or extra-cellular molecules and fragments, viruses, viral molecules and fragments, bacteria, and the like. In certain embodiments, the analytes are exogenous natural or synthetic compounds such as small molecules like drugs, prodrugs, and metabolites thereof. In certain embodiments, the analytes are nucleic acids such as proviral and/or viral DNA and/or RNA such as, for example, proviral and/or viral nucleic acids from human immunodeficiency virus (HIV), hepatitis B virus (HBV), hepatitis C virus (HCV), influenza, parvovirus B19, or any other human or animal viral pathogen. In certain embodiments, the analytes are viral particles for determining viral load. In certain embodiments, the analytes are biological markers for determining HLA blood types, useful for molecular diagnostic genotyping. In certain embodiments, the analytes are inflammatory biomarkers such as CXCL9/MIG and CXCL10/IP-10. In certain embodiments, the analytes are micronutrients such as Folic Acid, Homocysteine, Retinol Binding Protein (and/or Vitamin A), Thyroglobulin, Vitamin D, trace metals (e.g. zinc), Ferritin, Transferrin Receptors, Methylmalonic Acid, Holo-Transcobalamin, C-Reactive Protein, and alpha-Acid Glycoprotein.

"Biological specimen" refers to biologic samples, either in liquid or solid form, having contained therein an analyte of interest. A biological specimen can be, for example, whole blood, plasma, serum, lymph, synovial fluid, bone marrow, cerebrospinal cord fluid, semen, saliva, urine, feces, sputum, vaginal lavage, skin scrapings, hair root cells, or the like of humans or animals; physiological and pathological body liquids such as secretions, excretions, exudates and transudates; any cells or cell components of humans, animals, plants, bacteria, fungi, plasmids, viruses, parasites, or the like that contain analytes of interest, and any combination thereof. In certain embodiments, a biological specimen can be a human body fluid such as whole blood, which can contain analytes of interest such as proviral nucleic acids and/or plasma proteins such as Troponin, monoclonal kappa and lambda free light chains, Cystatin C, and Carbohydrate-Deficient Transferrin (CDT).

"Liquid biological specimen" means a biological fluid or a biological specimen suspended in a fluid medium (e.g. water, saline, etc.). Exemplary liquid biological specimens include human, animal, plant, bacteria, fungi, plasmids, viruses, parasites (e.g. helminthes, protozoas, spirochetes) extracts or suspensions; liquid extracts or homogenates of human or animal body tissues (e.g., bone, liver, kidney, brain); media from DNA or RNA synthesis; mixtures of chemically or biochemically synthesized DNA or RNA; and body fluids/liquids such as whole blood, plasma, serum, synovial fluid, cerebrospinal cord fluid, semen, and saliva.

I. Devices

Figure 1B:
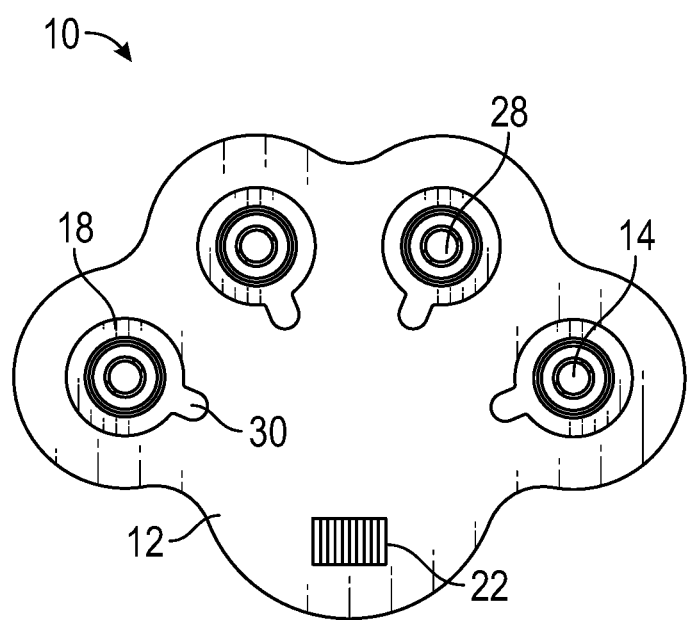
Figure 2:
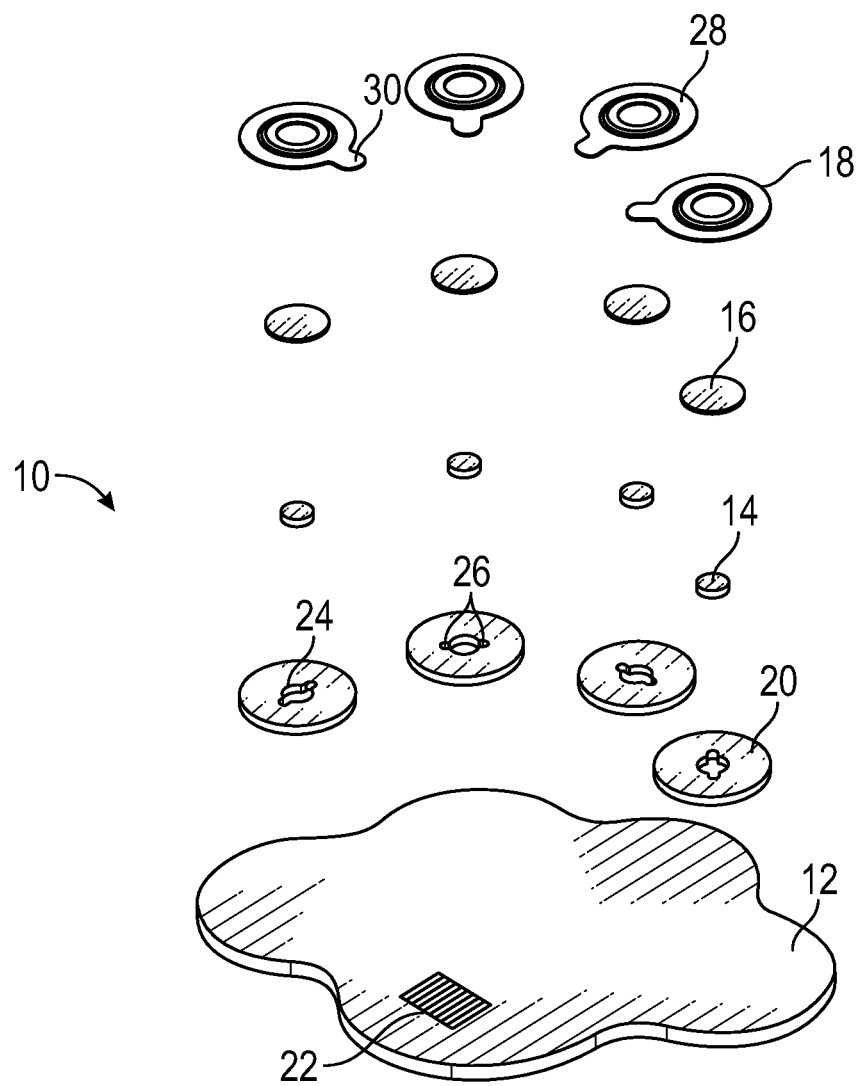
FIG. 2 shows an exploded view of a liquid specimen separation device in accordance with one example embodiment of the disclosure.
Figure 3A:
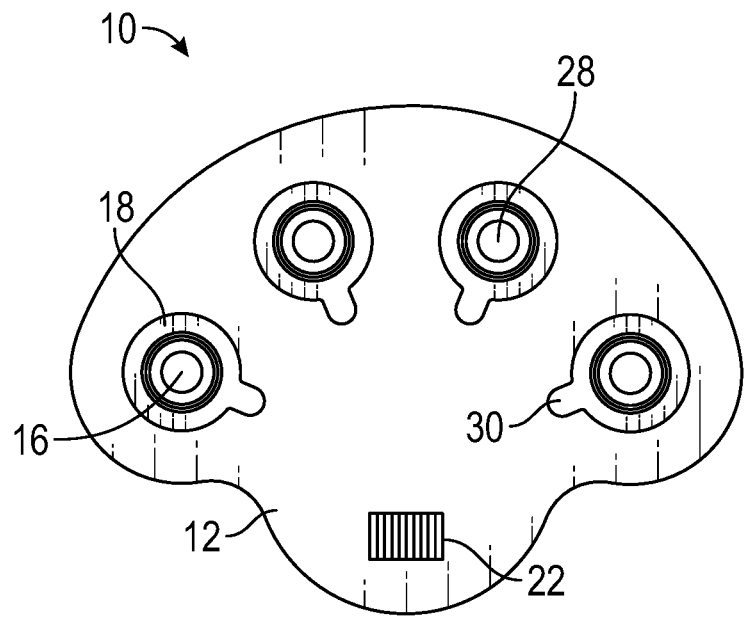
FIGS. 3A-3B show a liquid specimen separation device in accordance with a second example embodiment of the disclosure.
Figure 3B:
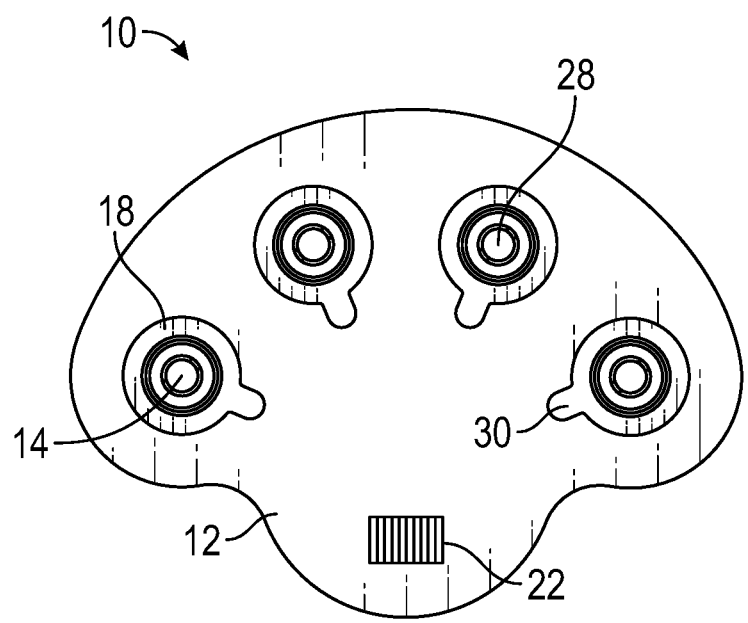
Figure 4A:
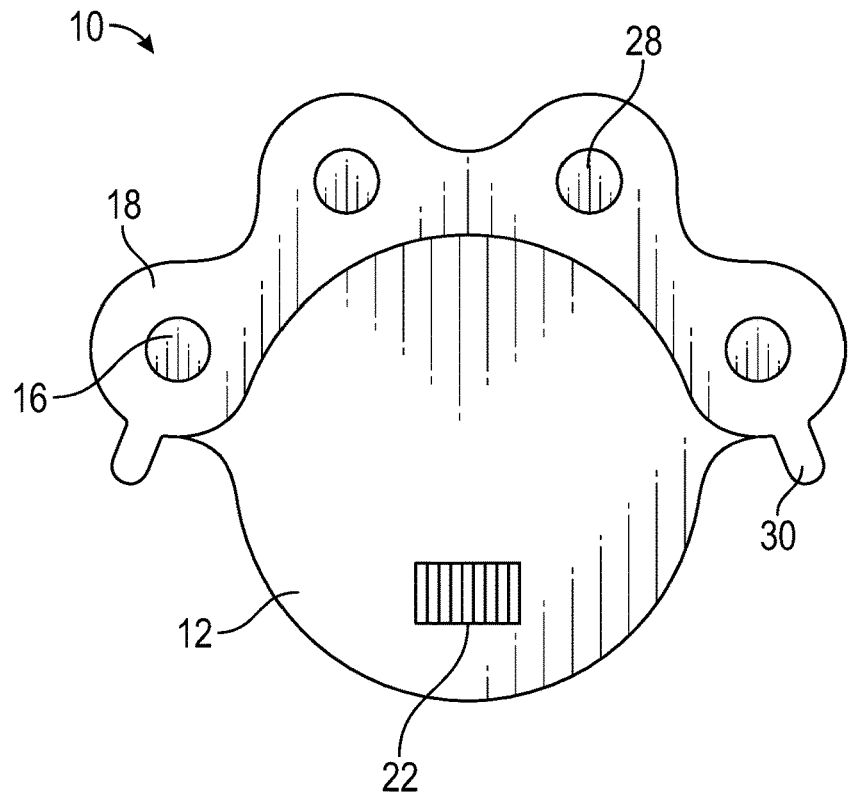
FIGS. 4A-4B show a liquid specimen separation device in accordance with a third example embodiment of the disclosure.
Figure 4B:
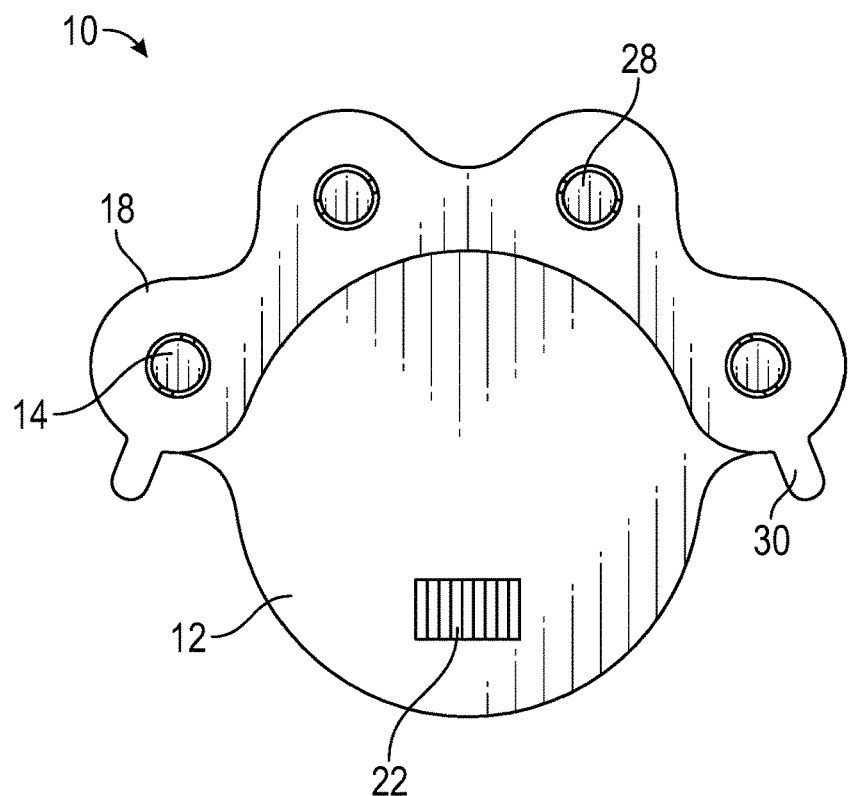
Figure 5:
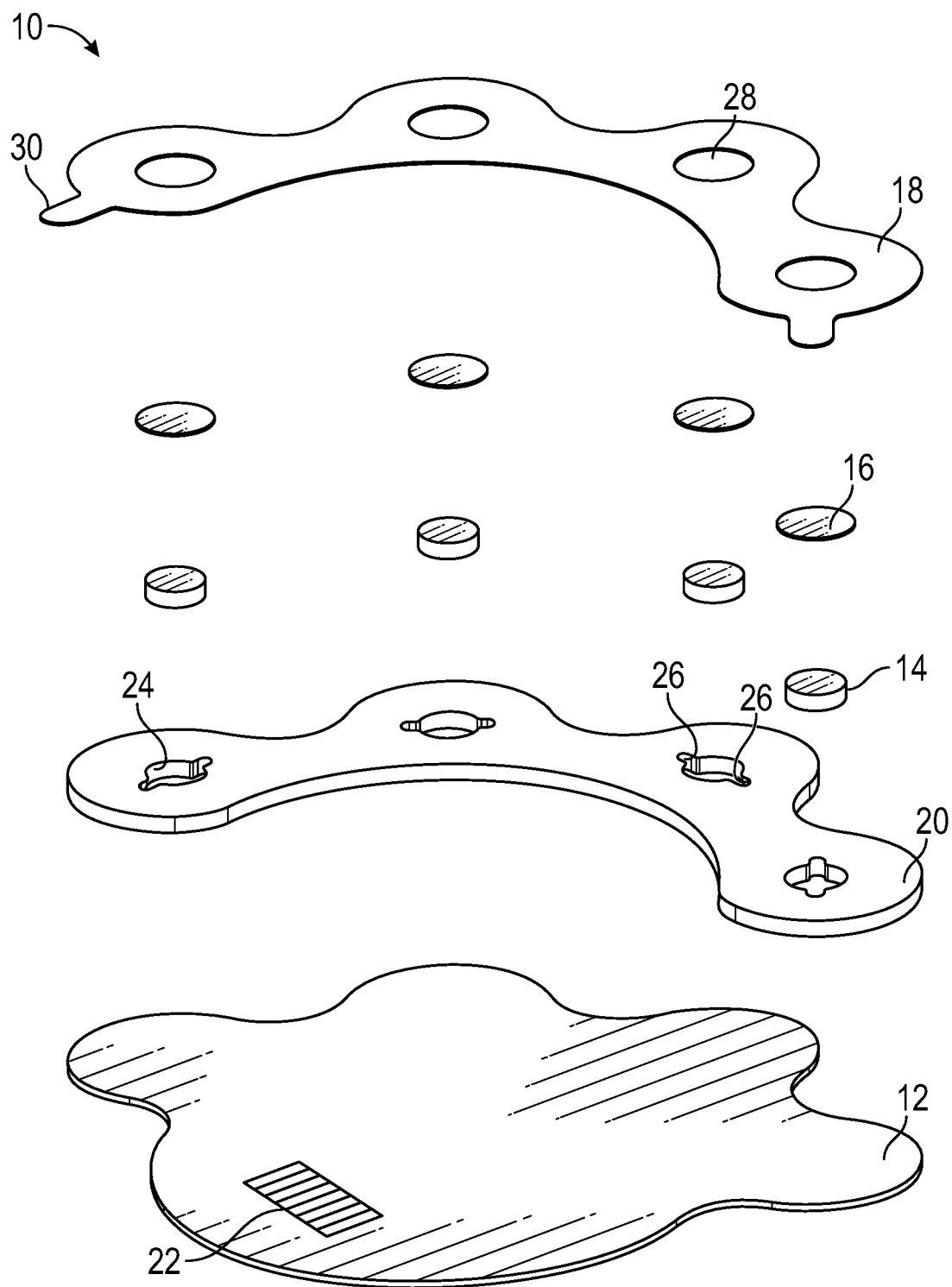
FIG. 5 shows an exploded view of a liquid specimen separation device in accordance with a third example embodiment of the disclosure.
Figure 6:
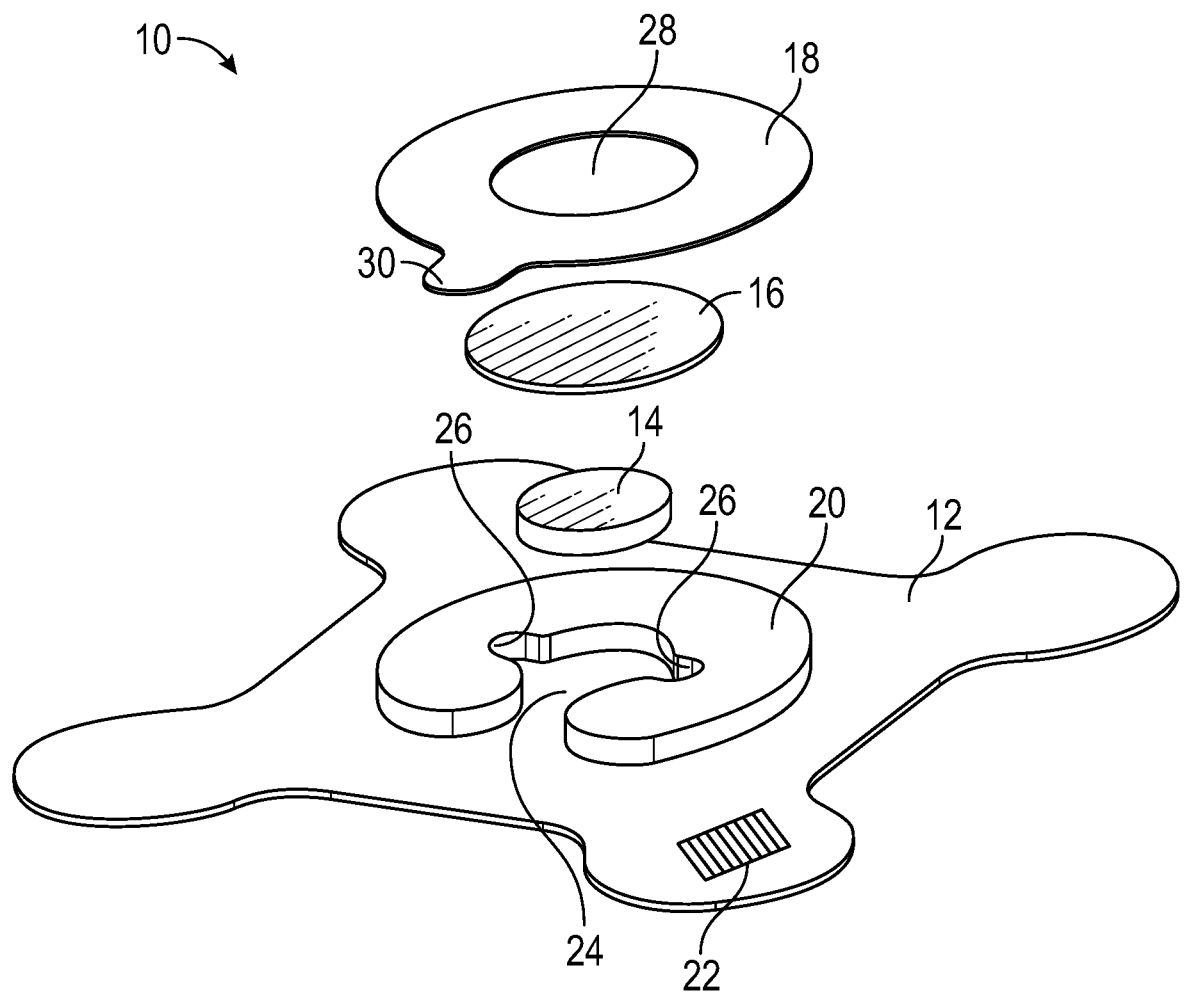
FIG. 6 shows an exploded view of a liquid specimen separation device in accordance with a fourth example embodiment of the disclosure.
Figure 7:
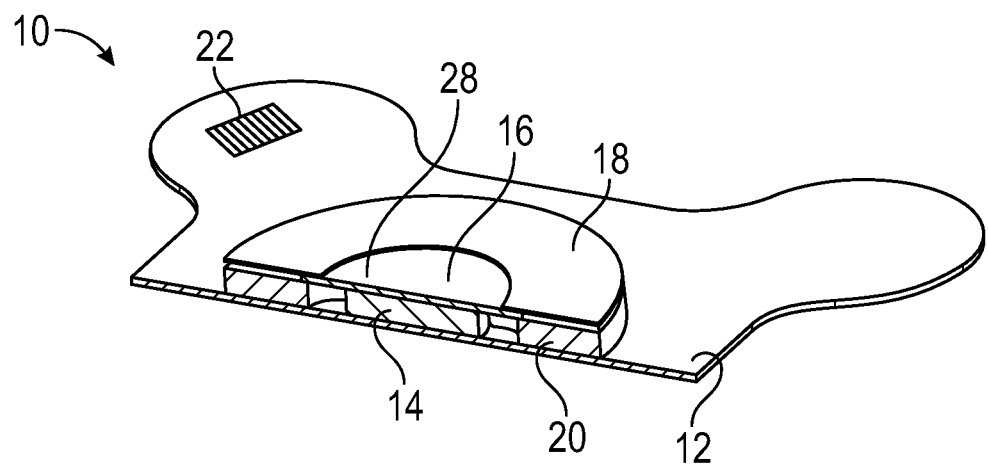
FIG. 7 shows cut away view of a liquid specimen separation device in accordance with a fourth example embodiment of the disclosure.
Figure 8:
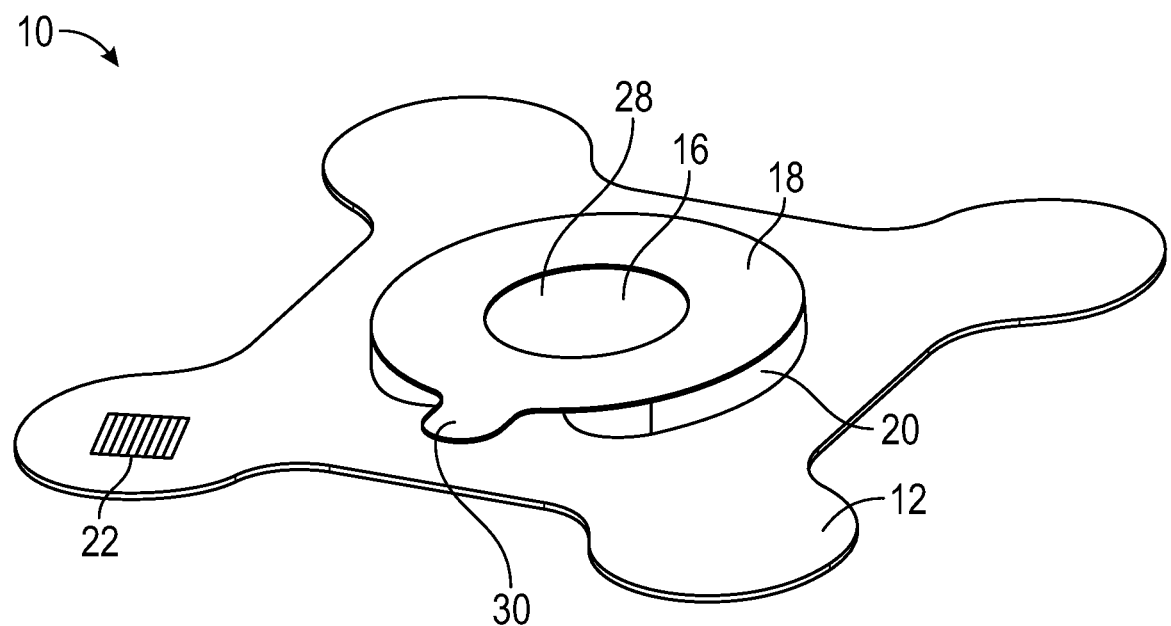
FIG. 8 shows a liquid specimen separation device in accordance with a fourth example embodiment of the disclosure.
Figure 9A:
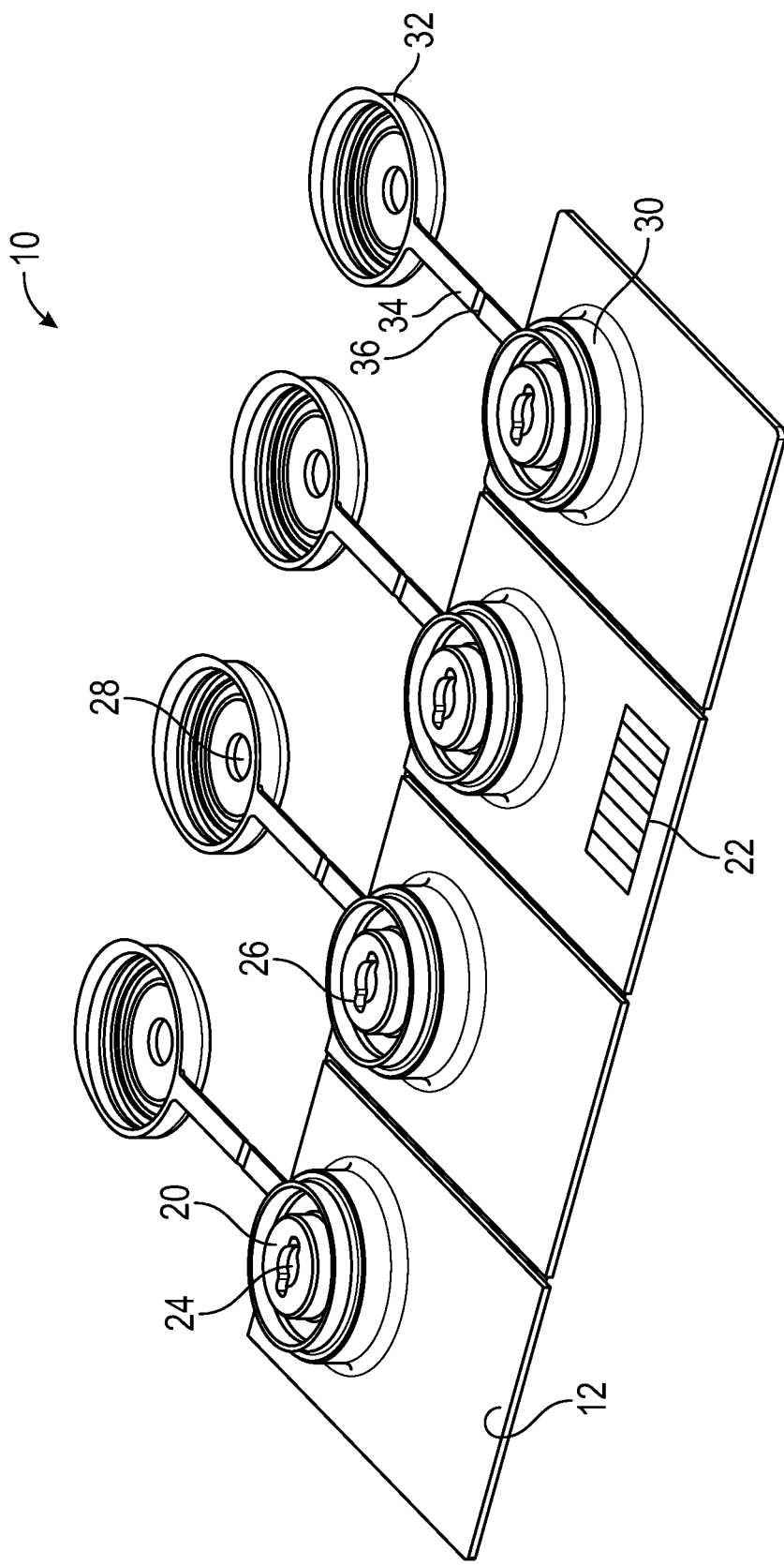
FIGS. 9A-9D show a liquid specimen separation device in accordance with a fifth example embodiment of the disclosure.
Figure 9B:
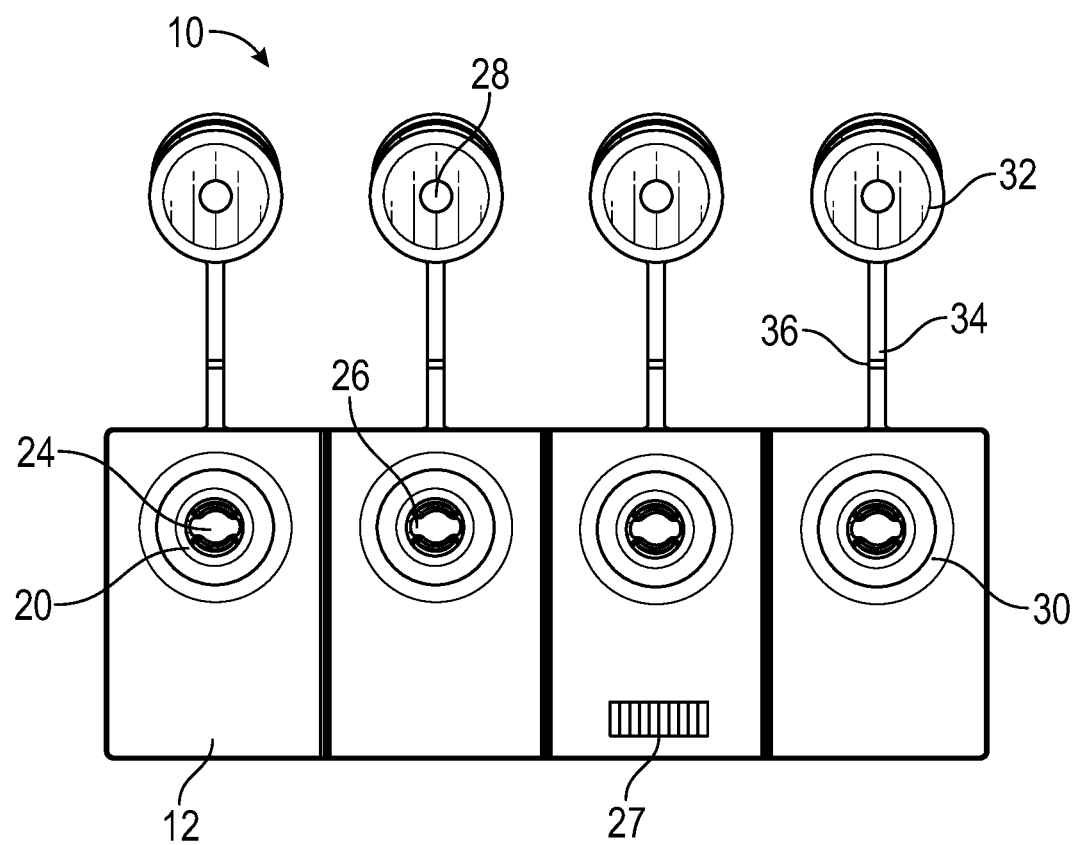
Figure 9C:
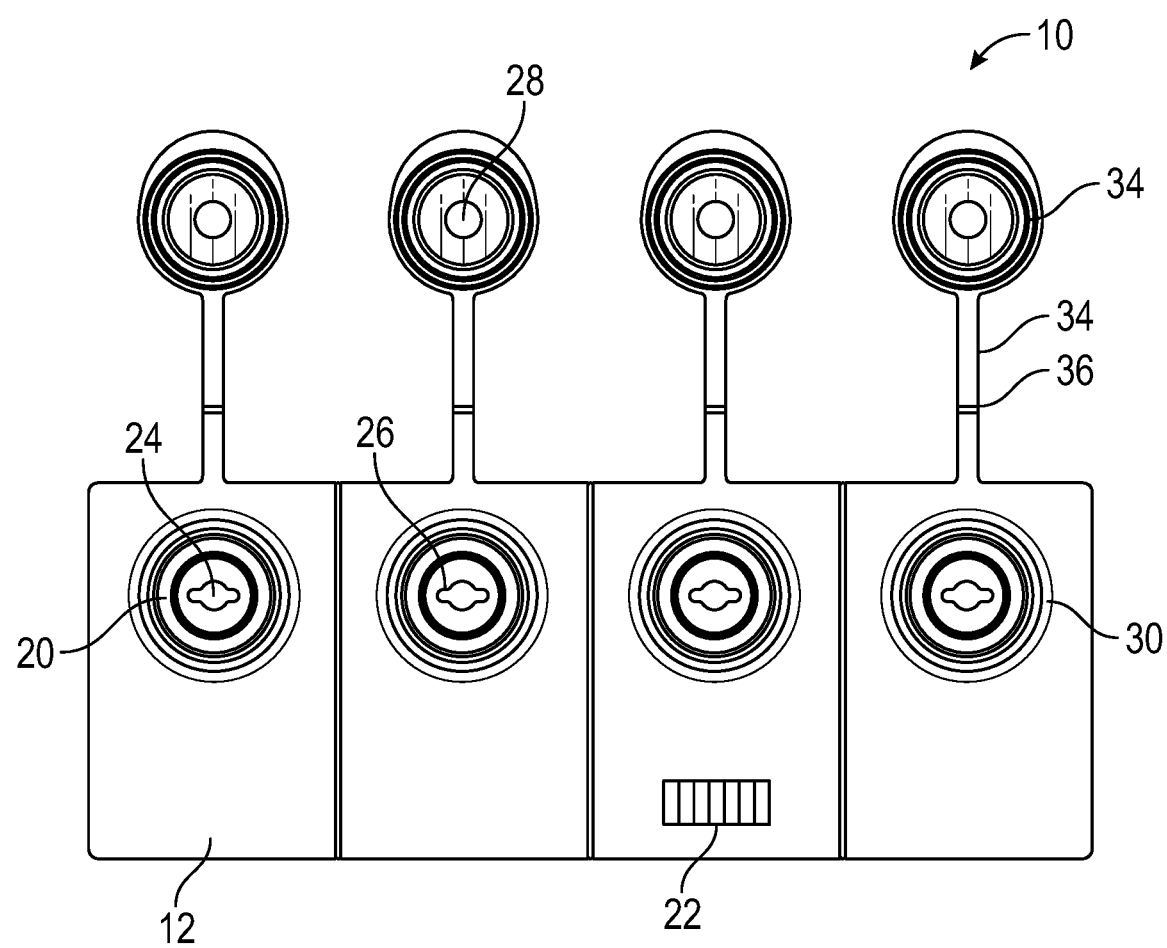
Figure 9D:
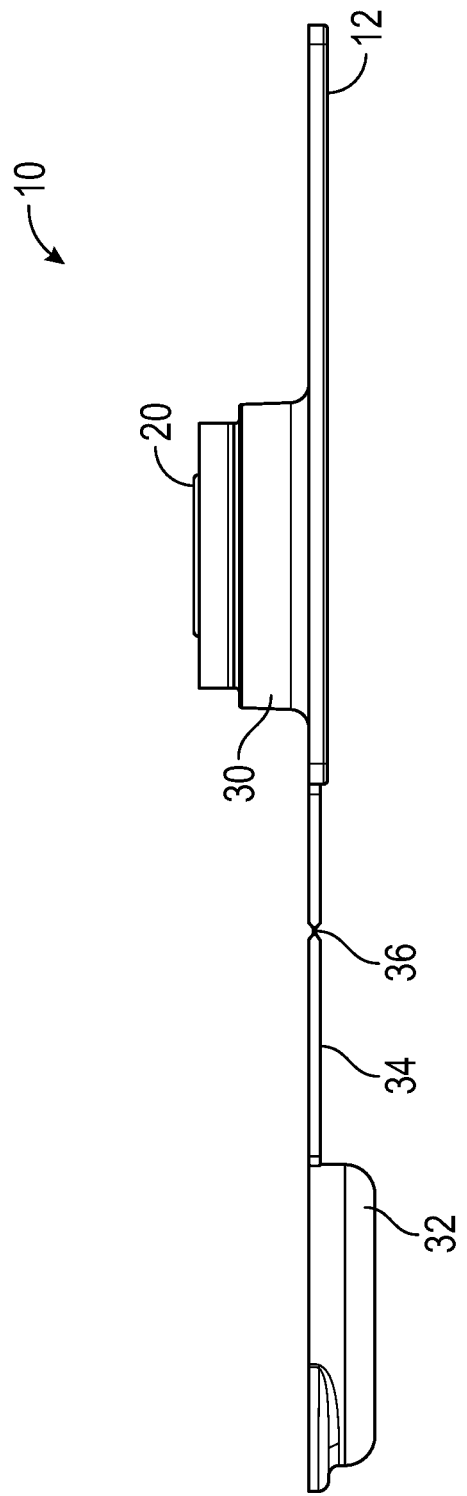
Figure 10A:
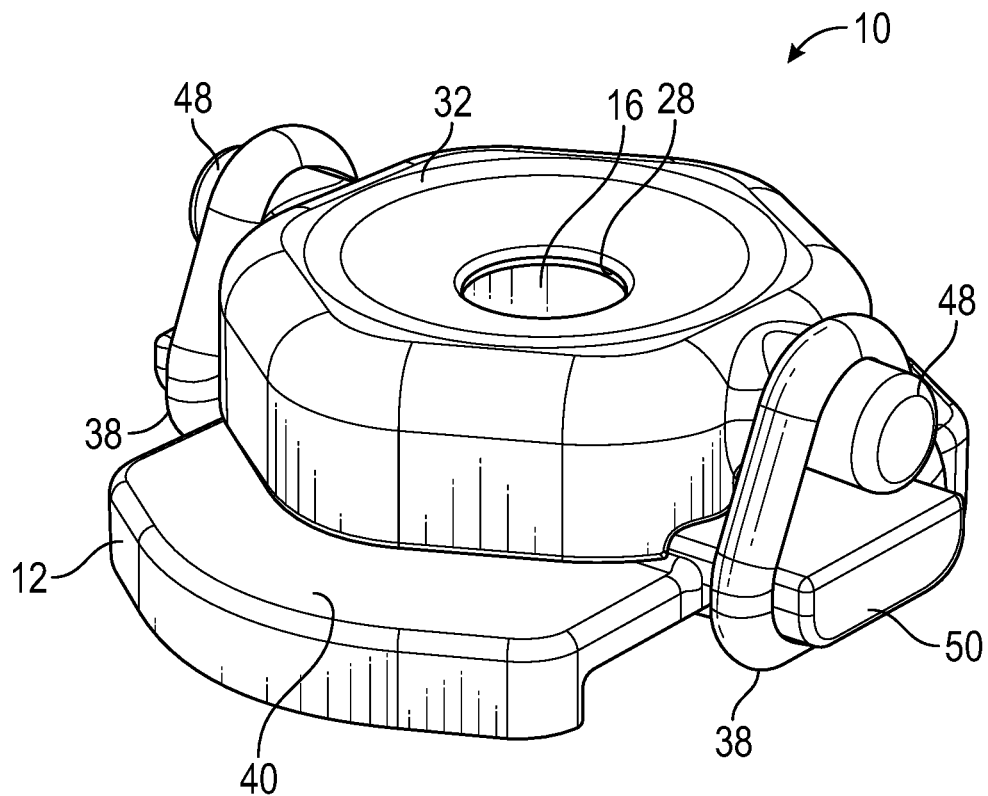
FIGS. 10A-10B show a liquid specimen separation device in accordance with a sixth example embodiment of the disclosure.
Figure 10B:
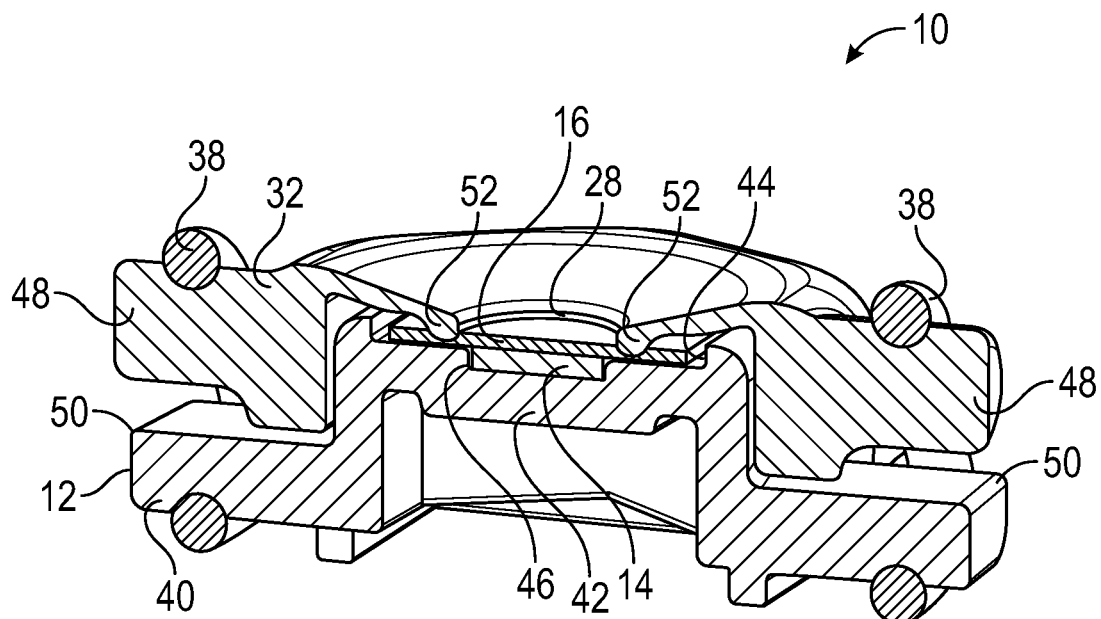
Figure 11A:
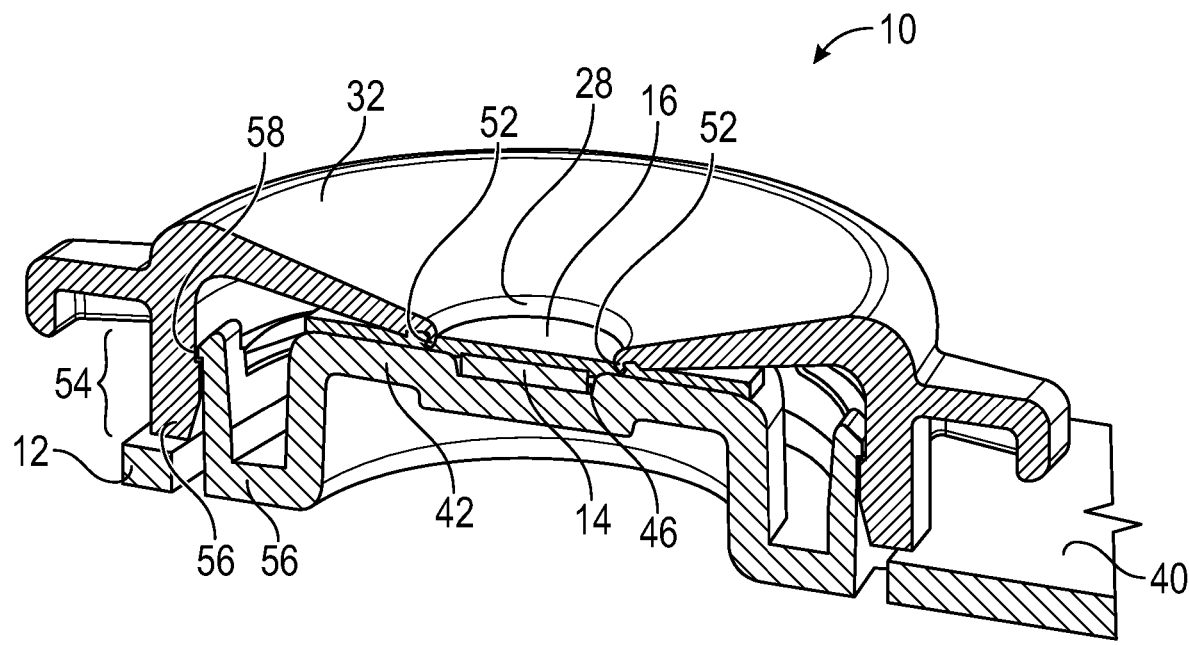
FIGS. 11A-11F show a liquid specimen separation device in accordance with a seventh example embodiment of the disclosure.
Figure 11B:
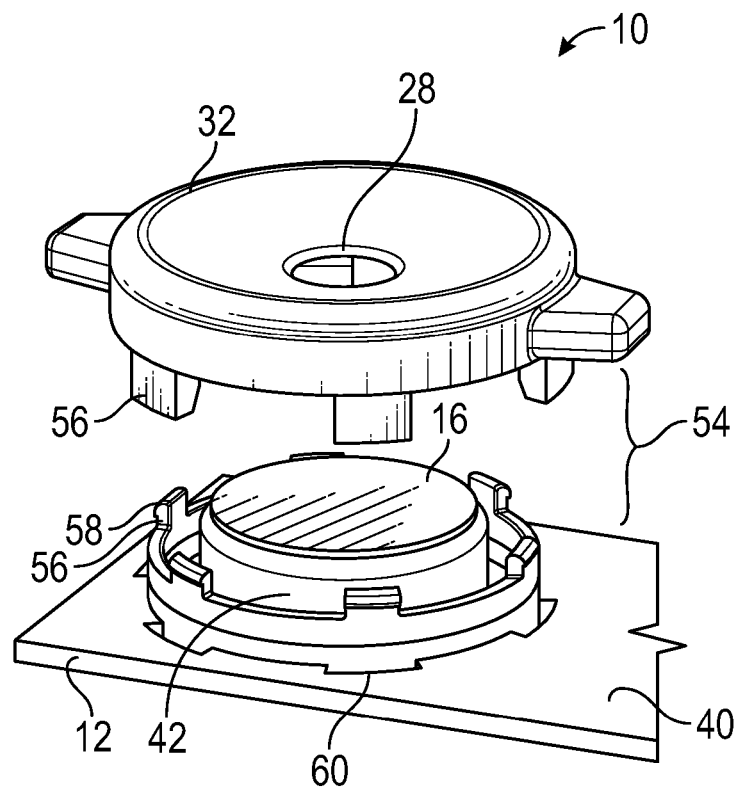
Figure 11C:
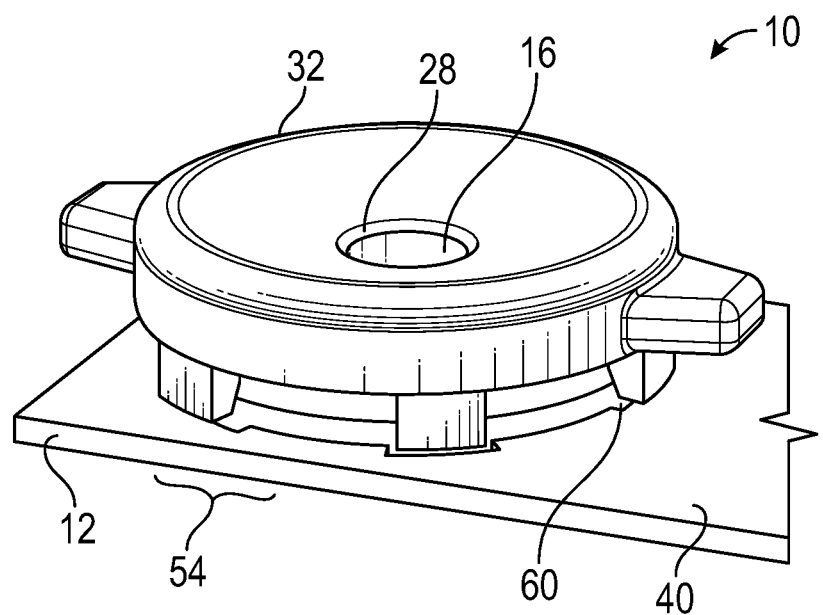
Figure 11D:
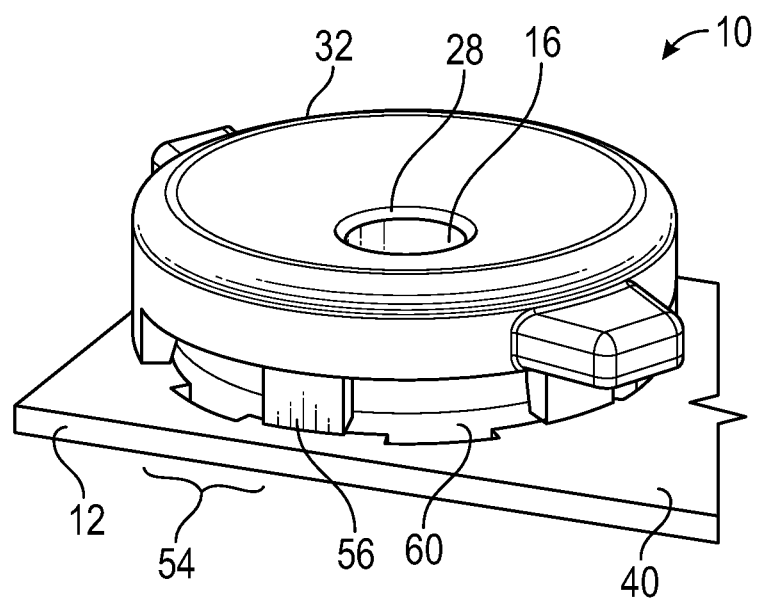
Figure 11E:
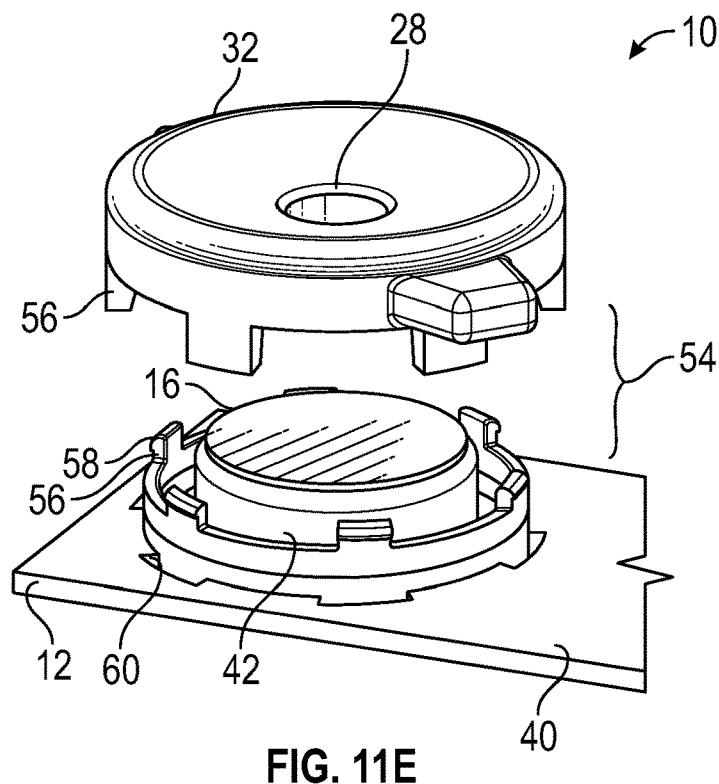
Figure 11F:
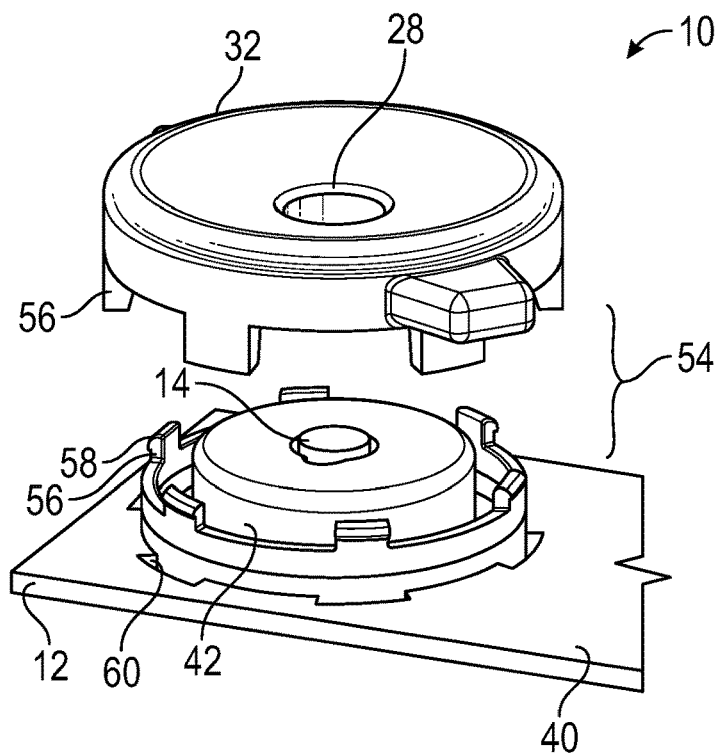

Embodiments of liquid biological specimen separation devices provided herein generally comprise a base support, one or more collection membranes disposed on the base, one or more separation membranes disposed on the collection membranes, and one or more covers disposed on the one or more separation membranes, as illustrated by the non-limiting embodiments shown in FIGS. 1A-11F. One embodiment of a liquid biological specimen separation device is illustrated in FIGS. 1A-2. Another embodiment of a liquid biological specimen separation device is illustrated in FIGS. 3A-3B. Another embodiment of a liquid biological specimen separation device is illustrated in FIGS. 4A-5. Another embodiment of a liquid biological specimen separation device is illustrated in FIGS. 6-8. Another embodiment of a liquid biological specimen separation device is illustrated in FIGS. 9A-9D. Another embodiment of a liquid biological specimen separation device is illustrated in FIGS. 10A-10B. Another embodiment of a liquid biological specimen separation device is illustrated in FIGS. 11A-11F.

FIGS. 1A-11F show a liquid biological specimen separation device 10. The separation device 10 can include base 12, collection membrane(s) 14, separation membrane(s) 16, cover(s) 18, collection membrane support(s) 20, and/or cap(s) 32.

Base 12 generally functions as a supporting surface. Base 12 can also function to secure the base 12, collection membranes 14, separation membranes 16, covers 18, and/or collection membrane supports 20 together. Base 12 can also serve as a protective enclosure that protects any components that may be contained therein (e.g. collection membranes 14, separation membranes 16, covers 18, collection membrane supports 20, biological specimens, and/or analytes enclosed by base 12) from outside influences or effects.

Base 12 can assume any dimensions, size, and shape suitable for serving as a support in a liquid biological specimen separation device 10. For example, the general shape of base 12 can be round, rectangular, oval, square, trapezoidal, triangular, pentagonal, hexagonal, octagonal, ellipsoid, crescent, curvilinear, egg, quatrefoil, cinquefoil, and the like. Base 12 can have a uniform shape. Base 12 can have a shape that includes one or more lobes/projections extending therefrom. Base 12 can have surfaces that are uniformly flat. Base 12 can be entirely flat. Base 12 can have a three dimensional, freeform structure. Base 12 can have one or more recesses dimensioned to receive, or projections dimensioned to extend into, and complementary fit collection membrane(s) 14, separation membrane(s) 16, cover(s) 18, collection membrane support(s) 20, and/or caps 32. Base 12 can have a projection extending therefrom shaped and dimensioned to receive or contain collection membrane(s) 14, separation membrane(s) 16, cover(s) 18, collection membrane support(s) 20, and/or caps 32.

Base 12 can have complementary features that permit separation device 10 to have an open configuration and a closed configuration. For example, base 12 can have a well portion and a cap portion that assume a first position wherein the well portion and the cap portion extend away from one another (open configuration) and a second position wherein the well portion and the cap portion complementary mate with one another (closed configuration). As another example, base 12 can have a raised inner projection and a cap that assume a first position wherein the raised inner projection and the cap are separated from one another (open configuration) and a second position wherein the raised inner projection and the cap complementary mate with one another (closed configuration).

Base 12 can have one or more sample deposition apertures 28 therethrough that define an area for depositing a liquid biological specimen. Base 12 can have features that improve handling and/or use of separation device 10. For example, base 12 can include features, projections, tabs, handles, and the like that facilitate gripping, holding, and manipulating separation device 10 (e.g. a tab for use in opening separation device 10 when in a closed configuration).

Separation device 10 can have any suitable number of biological specimen receiving/separation/collection regions such as 1, 2, 3, 4, 5, 6, 7, 8, 9, 10, 11, 12, 13, 14, 15, 16, 17, 18, 19, 20 or more such regions.

Base 12 can be made of any suitable material, preferably one that provides sufficient flexibility/stiffness and strength. Base 12 can be made of, for example, suitable plastics materials (e.g. polyethylene, acrylic, polypropylene), paper materials (e.g. cardstock, cardboard, etc.), and the like.

Base 12 can include an identifier 22 thereon or therein. The identifier 22 can be integrated/disposed into or onto an outer surface of base 12. For example, identifier 22 can be printed on or attached (e.g. adhesive label) to base 12. The identifier 22 can also be integrated/disposed in base 12. The identifier 22 can use any suitable identification technology. For example, identifier 22 can be any suitable RFID chip, single-dimensional (1D) barcodes, two-dimensional (2D) barcodes, QR codes, alpha-numeric codes, and the like.

Identifier 22 can store or have associated therewith identification information. Identification information can include information specific to a patient associated with a biological specimen stored therein, including personal information (address, name, sex, date of birth, ethnic background, etc.) and/or biometric information (e.g., a fingerprint, a facial image or template). Identifier 22 can also store or have associated therewith contextual information such as time, date, location of testing, and the like. To protect identifier 22 and any information associated therewith, a layer of overlaminate or other protective material may additionally be provided over identifier 22.

One or more collection membranes 14 can be disposed on base 12. One or more collection membrane supports 20 can also be disposed on base 12. A collection membrane 14 can be disposed in a collection membrane support 20. The collection membranes 14 generally function to absorb the fraction of a liquid biological specimen that flows through separation membrane 16. The collection membrane supports 20 generally function to support (e.g. hold in place) the collection membranes 14.

Collection membranes 14 can be reversibly adhered to or held in place on base 12 by any suitable means. For example, collection membrane 14 can be secured in place by cover 18 (e.g. a sticker), the sticker being adhered to base 12 and having sandwiched there between collection membrane 14. As another example, collection membrane 14 can be secured in place by an interference fit with another feature of separation device 10 (e.g. the collection membrane 14 is disposed in, and has an interference fit with, a well in base 12). As another example, collection membrane 14 can be secured in place by disposing collection membrane 14 in a recess of base 12 dimensioned to fit and receive collection membrane 14. As another example, collection membrane 14 can be secured in place by securing collection membrane 14 in between a well portion and a cap portion of base 12 that complementary mate with one another (a closed configuration). The collection membrane 14 can be secured in between the well portion and the cap portion of base 12 along with other features (e.g. separation membrane 16), and the stacked features can be collectively dimensioned to prevent or reduce movement of the features within or out of separation device 10. As another example, collection membrane 14 can be secured in place by securing collection membrane 14 in between a raised inner projection of base 12 and a cap 32 that complementary mate with one another (a closed configuration). The collection membrane 14 can be secured in between a raised inner projection of base 12 and a cap 32 along with other features (e.g. separation membrane 16), and the stacked features can be collectively dimensioned to prevent or reduce movement of the features within or out of separation device 10.

As another example, in embodiments that include collection membrane supports 20, collection membranes 12 can be connected or attached to collection membrane supports 20, the collection membrane supports 20 being adhered to, fixedly attached to, or held in place on, base 12 by any suitable means (e.g. adhesives, interference fit into a well of the base). A benefit of this approach is that collection membranes 14 can be easily separated from both base 12 and collection membrane supports 20. For example, the interface between a collection membrane 14 and a collection membrane support 20 can include a series of perforations that enable easy removal of collection membrane 14 from collection membrane support 20. This facilitates further processing of the biological specimen and/or analytes of interest absorbed by collection membrane 14.

In embodiments having both collection membrane(s) 14 and collection membrane support(s) 20, the collection membranes 14 and collection membrane supports 20 can be a unitary item (e.g. a single piece of whatman 903 paper having a sample collection region and a supporting region) or discrete items from one another (e.g. a first piece of whatman 903 paper is a collection membrane and a second piece of whatman 903 paper is a collection membrane support).

The collection membrane(s) 14 and collection membrane support(s) 20 can be made of the same material or different materials. The collection membranes 14 and collection membrane supports 20 can be made of any suitable material. Suitable materials include, for example, plastics, polymers, cotton, cellulose, and/or paper. In some embodiments, the collection membrane(s) 14 and/or collection membrane support(s) 20 are filter papers. Filter papers that may be selected for use include cellulose fiber papers manufactured from cotton linters. Cotton linters (i.e., cotton wool) are short fibers that adhere to seeds of a cotton plant after the longer fibers have been pulled from the cotton seed. Filter papers can also include filter papers for blood collection registered by the U.S. Food and Drug Administration as Class II Medical Devices (21 CFR § 862.1675), such as WHATMAN 903, AHLSTROM 142, AHLSTROM 226, AHLSTROM 222, AHLSTROM 238, AHLSTROM 270, ALHSTROM 601, and ESSENTRA. In some embodiments, a majority of the cellulose fibers of a cellulose fiber filter paper may have sizes in the range of about 1-100 microns, 10-50 microns, or 20-25 microns in length and may contain numerous hydrophobic and/or hydrophilic pockets.

Collection membranes 14 and collection membrane supports 20 can have any suitable shape such as, for example, a circle, oval, square, rectangle, triangle, hexagonal, or other shapes and surface textures suitable for use in the devices described herein. Collection membrane support 20 can have a collection membrane aperture 24 for receiving collection membranes 14. Collection membranes 14 and collection membrane supports 20 can also be dimensioned in a manner that facilitates removing collection membranes 14 from collection membrane supports 20. For example, collection membrane supports 20 can include removal apertures 26 that allow a device (e.g. tongs) to selectively pincer and remove collection membranes 14 from collection membrane supports 20.

Separation device 10 can include one or more collection membranes 14 and/or one or more collection membrane supports 20. For example, separation device 10 can include 1, 2, 3, 4, 5, 6, 7, 8, 9, 10, 11, 12, 13, 14, 15, 16, 17, 18, 19, 20 or more collection membranes 14 and/or collection membrane supports 20. The number of collection membranes 14 and the number of collection membrane supports 20 in separation device 10 can be the same or they can be different. For example, in some embodiments separation device 10 can have four collection membranes 14 and four collection membrane supports 20 while in other embodiments separation device 10 can have four collection membranes 14 and one collection membrane support 20.

Collection membranes 14 and/or collection membrane supports 20 can have any suitable size. In certain embodiments, collection membranes 14 and/or collection membrane supports 20 can have a diameter/width of from about 1 mm to 50 mm, or from 10 mm to 30 mm, inclusive. In some embodiments, collection membranes 14 have a diameter/width of from about 1 mm to about 15 mm.

Collection membranes 14 can include a composition absorbed to a surface thereof, wherein the composition protects against degradation of an analyte of interest disposed therein. Protection against degradation may include protection against substantial damaging of analytes of interest caused by chemical or biological agents including action of bacteria, free radicals, nucleases, ultraviolet radiation, oxidizing agent, alkylating agents, or acidic agents (e.g., pollutants in the atmosphere). In certain embodiments, the composition absorbed on the collection membrane 14 can include one or more of a weak base, a chelating agent, a protein denaturing agent such as a detergent or surfactant, a nuclease inhibitor, a free radical trap, and an oxygen scavenger element. As used herein, a "weak base" can be a Lewis base which has a pH of about 6 to 10, preferably about pH 8 to 9.5. In a case where the stored analyte of interest is RNA, particularly unstable RNA, the composition may include RNase inhibitors and inactivators, genetic probes, complementary DNA or RNA (or functionally equivalent compounds), proteins and organic moieties that stabilize RNA or prevent its degradation.

One or more separation membranes 16 can be disposed on base 12, collection membranes 14, covers 18 and/or collection membrane supports 20. The separation membranes 16 generally function to separate a liquid biological specimen into a first fraction and a second fraction. The first fraction is contained/trapped within separation membranes 16 while the second faction passes through separation membranes 16 and into collection membranes 14.

Separation membranes 16 can be reversibly held in place on base 12, collection membranes 14, covers 18, and/or collection membrane supports 20 by any suitable means. For example, separation membranes 16 can be secured in place by cover 18 (e.g. a sticker), the sticker being adhered to base 12 and/or collection membrane supports 20 and having sandwiched there between collection membranes 14, collection membrane supports 20, and/or separation membranes 16. The compressive force keeps separation membranes 16 in contact with collection membranes 14. In another example, separation membranes 16 can be secured in place by cover 18 (e.g. a sticker), the sticker being adhered to base 12 and having sandwiched there between separation membranes 16. In another example, separation membranes 16 can be secured in place by an interference fit with another feature of separation device 10 (e.g. the separation membrane 16 is disposed in, and has an interference fit with, a well in base 12). As another example, separation membrane 16 can be secured in place by disposing separation membrane 16 in a recess of base 12 dimensioned to fit and receive separation membrane 16.

As another example, separation membrane 16 can be secured in place by securing separation membrane 16 in between a well portion and a cap portion of base 12 that complementary mate with one another (a closed configuration). The separation membrane 16 can be secured in between the well portion and the cap portion of base 12 along with other features (e.g. collection membrane 14), and the stacked features can be collectively dimensioned to prevent or reduce movement of the features within or out of separation device 10. As another example, separation membrane 16 can be secured in place by securing separation membrane 16 in between a raised inner projection of base 12 and a cap 32 that complementary mate with one another (a closed configuration). The separation membrane 16 can be secured in between a raised inner projection of base 12 and a cap 32 along with other features (e.g. collection membrane 14), and the stacked features can be collectively dimensioned to prevent or reduce movement of the features within or out of separation device 10.

Both collection membranes 14 and separation membranes 16 are easily separable from separation device 10 so that collection membranes 14 and separation membranes 16 can be accessed and removed from separation device 10 for further analysis.

Separation membranes 16 are generally made of a material that allows for flow of a liquid biological specimen or a fraction thereof therethrough. Separation membranes 16 can comprise a plurality of fibers. Separation membranes 16 can be made of a material that has a gradually decreasing pore size (e.g. an asymmetric porous membrane) from a top side (e.g. the side where biological specimens are initially deposited) to a bottom side (the side in contact with collection membrane 14). Separation membrane 16 can also be made of a material that has a uniform pore size throughout. In certain embodiments, flow of a liquid biological specimen deposited on separation membrane 16 through separation membrane 16 is driven by capillary forces (e.g. capillary flow) and/or gravity. In certain embodiments, materials suitable for use in separation membranes 16 are those in which one biological specimen moves faster through the separation membrane than another biological specimen (e.g. blood plasma moves faster than corpuscles).

Suitable materials for use in separation membranes 16 can include, for example, synthetic polymers having fine fiber diameter and fibers made of glass or porous polymers. In certain preferred embodiments, separation membranes 16 are made of a polysulfone polymer material having a porosity that gradually decreases from a top side of the membrane to a bottom side of the membrane so as to filter and trap solid and/or liquid components of a liquid biological specimen deposited on separation membranes 16. Separation membrane materials can include, for example, synthetic or natural polymers such as cellulose mixed esters, polyvinylidene difluoride, polytetrafluoroethylene, polycarbonate, polypropylene, polyester, and polysulfone polymers and matrices (e.g., asymmetric sub-micron polysulfone (BTS) and/or asymmetric super micron polysulfone (MMM) made by Pall Corporation). Separation membrane materials can also include, for example, VIVID GR, VIVID GX, and CYTOSEP 1660. A person of ordinary skill will readily appreciate that other membranes or filtering materials can be used. In some embodiments, separation membranes 16 are suitable for blood component filtering and serum/plasma separation. In some embodiments, separation membranes 16 have a porosity of not more than 30%, and preferably not more than 25%. In certain embodiments, separation membranes 16 can be made of polysulfone polymer having a pore size ranging from about 0.1-20 microns and a pore size ratio from about 50:1 to 100:1.

The size of a separation membrane 16 can be larger than the size of a collection membrane 14 to which it is removably disposed upon. For example, the size of a separation membrane 16 may be at least 20%, or at least 30%, or at least 40%, or at least 50% larger than a size of a corresponding collection membrane 14. Alternatively, the size of a separation membrane 16 can be the same or about the same (e.g. within 10% by area) size as a collection membrane 14 to which it is removably disposed upon. Alternatively, the size of a separation membrane 16 can be smaller than the size of a collection membrane 14 to which it is removably disposed upon. In certain embodiments, a separation membrane 16 has a diameter/width of from about 1 mm to 50 mm, or from 10 mm to 30 mm, inclusive. For example, separation membrane 16 can have a diameter/width of about 10 mm to about 20 mm.

Separation membrane 16 can have a shape that is the same shape as a corresponding collection membrane 14 (e.g. circles). Separation membrane 16 can also have a shape that is different from a shape of a corresponding collection membrane 14 and, thus, does not align in its entirety with the shape of collection membrane 14 when brought into contact thereto. For example, separation membrane 16 can have an irregular or oblong shape (e.g., a racquet shape with a handle-like extension extending on a lateral side thereof) whereas collection membrane 14 can have a circular shape.

Separation device 10 can include one or more separation membranes 16. For example, separation device 10 can include 1, 2, 3, 4, 5, 6, 7, 8, 9, 10, 11, 12, 13, 14, 15, 16, 17, 18, 19, 20 or more separation membranes 16.

One or more covers 18 can be disposed on separation membranes 16, collection membranes 14, collection membrane supports 20, and/or base 12. The covers 18 generally have one or more sample deposition apertures 28 therethrough that define an area for depositing a liquid biological specimen. The covers 18 can also function to secure the separation membranes 16, collection membranes 14, collection membrane supports 20, and/or base 12 together. Covers 18 are reversibly adhered or attached to separation membranes 16, collection membranes 14, collection membrane supports 20, and/or base 12 by any suitable means. For example, covers 18 can be stickers having an adhesive side that is used to attach covers 18 to separation membranes 16, collection membranes 14, collection membrane supports 20, and/or base 12. Covers 18 are reversibly adhered so that covers 18 are easily removed in order to access and remove collection membranes 14 and/or separation membranes 16 from separation device 10 for further processing and analysis.

Covers 18 can include one or more projections 30 that make removal of covers 18 easier. For example, covers 18 can have a graspable tab to facilitate removal of covers 18 from separation device 10.

Separation device 10 can also include a desiccant for drying, or keeping dry, a biological specimen. The desiccant can be disposed anywhere on separation device 10 (e.g. on or in base 12).

Separation device 10 can include one or more caps 32. Caps 32 generally have one or more sample deposition apertures 28 therethrough that define an area for depositing a liquid biological specimen. Caps 32 can operate to removably secure the separation membranes 16, collection membranes 14, and/or base 12 together. Caps 32 can be reversibly attached to base 12 by any suitable means. For example, separation device 10 can include elastomeric band fasteners 38 that urge and hold base 12 and caps 32 together. As another example, base 12 can be secured to cap 32 by a twist-lock mechanism 54 that urges and holds base 12 and caps 32 together. Caps 32 can be made of, for example, suitable plastics materials (e.g. polyethylene, acrylic, polypropylene).

FIGS. 1A-2 show a liquid biological specimen separation device 10 in accordance with one embodiment of the invention. The liquid biological specimen separation device 10 has a base 12. Base 12 is a flat bifacial sheet having a uniform thickness and a modified cinquefoil shape defined by a series of radial projections extending therefrom. The largest radial projection is a handle that facilitates handling/holding separation device 10. Each of the four remaining radial projections provide a supporting surface or region for a corresponding one of the biological specimen receiving/separation/collection regions.

Disposed on liquid biological specimen separation device 10 are four circular collection membrane supports 20 and corresponding circular collection membranes 14 disposed therein. Each of the four collection membrane supports 20 is separated from a corresponding collection membrane 14 by perforations, the perforations enabling easy removal of the collection membranes 14 from their respective collection membrane support 20. Each of the collection membrane supports 20 also includes two removal apertures 26 that enable the use of a device (e.g. tweezers or tongs) to selectively grasp and remove collection membranes 14 from their respective collection membrane support 20.

The liquid biological specimen separation device 10 has four circular separation membranes 16, each of which is disposed on a respective one of the collection membranes 14 and collection membrane supports 20. The circular separation membranes 16, when disposed on collection membranes 14, completely overlap the collection membranes 14 because the diameter of separation membranes 16 is larger than the diameter of collection membranes 14. The diameter of separation membranes 16, however, is smaller than the diameter of collection membrane supports 20.

The liquid biological specimen separation device 10 has four generally circular covers 18, each having a tab extending therefrom. The covers 18 are stickers, and each sticker is adhesively disposed on a respective one of the separation membranes 16 and collection membrane supports 20. Each sticker has a biological sample deposition aperture extending therethrough that permits depositing a liquid biological specimen onto the separation membrane 16 secured underneath the sticker.

FIGS. 3A-3B show a liquid biological specimen separation device 10 in accordance with another embodiment of the invention. The liquid biological specimen separation device 10 of FIGS. 3A-3B is substantially the same as the liquid biological specimen separation device 10 of FIGS. 1A-2 except that base 12 is a semi-circular shape having one radial projection extending therefrom, the radial projection serving as a handle for handling separation device 10.

FIGS. 4A-5 show a liquid biological specimen separation device 10 in accordance with another embodiment of the invention. The liquid biological specimen separation device 10 of FIGS. 4A-5 is similar to the liquid biological specimen separation device 10 of FIGS. 1A-2 with a few differences. As shown in FIGS. 4A-5, separation device 10 has one collection membrane support 20 and one cover 18. The collection membrane support 20 and cover 18 are generally shaped to match the portion of base 10 having the four radial projections. Cover 18 also has two tabs extending therefrom and projecting outwards from separation device 10.

FIGS. 6-8 show a liquid biological specimen separation device 10 in accordance with another embodiment of the invention. In this embodiment, base 12 is a generally square shape having four radial lobes projecting outwards from separation device 10, one projection at each corner. The liquid biological specimen separation device 10 includes one collection membrane 14, one collection membrane support 20, one separation membrane 16, and one cover 18.

FIGS. 9A-9D show a liquid biological specimen separation device 10 in accordance with another embodiment of the invention. The liquid biological specimen separation device 10 has a base 12. Base 12 is a made of a clear plastic material and has a flip top design. Base 12 has four wells 30 and four corresponding caps 32 that are designed to complementary mate with one another. Caps 32 are connected to the rest of base 12 by arms 34. Arms 34 have a hinge 36 that allows movement of caps 32 relative to wells 30. Base 12 can assume a first position wherein caps 32 extend away from wells 30 (e.g. an open configuration, as shown). Base 12 can assume a second position wherein caps 32 and wells 30 complementary mate with one another to form a closed configuration. Each cap 32 includes a sample deposition aperture 28 therethrough that defines an area for depositing a liquid biological specimen. Each cap 32 also includes a tab feature that facilitates opening separation device 10 when in a closed configuration.

Disposed in wells 30 of liquid biological specimen separation device 10 are four circular collection membrane supports 20. Circular collection membranes 14 (not shown) are disposable in a respective one of the collection membrane supports 20. Each of the collection membrane supports 20 includes two removal apertures 26 that enable the use of a device (e.g. tweezers or tongs) to selectively grasp and remove collection membranes 14 from their respective collection membrane support 20.

Four circular separation membranes 16 (not shown) are disposable in a respective one of the recesses in caps 32. Four generally circular covers 18 (not shown) are disposable on a respective one of the separation membranes 16. The covers 18 are stickers, and each sticker is adhesively disposed on a respective one of the separation membranes 16 and an internal surface of caps 32. Each sticker adheres a separation membrane 16 to an internal surface of a respective cap 32. Each sticker has a biological sample deposition aperture extending therethrough that permits flow from separation membrane 16 to collection membrane 14. In a closed configuration of separation device 10, at least a portion of separation membrane 16 comes into contact with collection membrane 14 (some contact between the two membranes can be intermediated by a cover 18).

FIGS. 10A-10B show a liquid biological specimen separation device 10 in accordance with another embodiment of the invention. The liquid biological specimen separation device 10 has a base 12. Base 12 is a made of a plastic material. Base 12 has a three dimensional shape comprising a relatively low profile outer periphery 40 and a raised inner projection 42. The raised inner projection 42 has a first recess 44 therein dimensioned to receive a separation membrane 16. The first recess 44 has a second recess 46 therein dimensioned to receive a collection membrane 14. Base 12 also has two fastening tabs 50 extending therefrom.

The liquid biological specimen separation device 10 has a cap 32. The cap 32 is dimensioned to complementary mate with raised inner projection 42. Cap 32 includes a funnel portion arranged to direct fluid flow towards a sample deposition aperture 28 extending through cap 32, the sample deposition aperture 28 defining an area for depositing a liquid biological specimen. Cap 32 has two diametrically opposing pegs 48 extending therefrom. Pegs 48 are positioned on cap 32 such that they are alignable with fastening tabs 50.

Disposed in the second recess 46 is a collection membrane 14. The second recess 46 and collection membrane 14 can be dimensioned such that collection membrane 14 sits flush with a top surface of the first recess 44. The second recess 46 and collection membrane 14 can be dimensioned such that that collection membrane 14 extends a short distance (e.g. 0.5 mm) above a top surface of the first recess 44. In either case, at least a portion of separation membrane 16 comes into contact with collection membrane 14.

Disposed in the first recess 44 is a separation membrane 16. Separation membrane 16, collection membrane 14, and cap 32 are aligned about an axis extending through a center point of each of the separation membrane 16, collection membrane 14, and cap 32.

The liquid biological specimen separation device 10 has two fasteners 38. Fasteners 38 are elastomeric bands wrappable around pegs 48 and fastening tabs 50 such that base 12 is secured to cap 32.

The liquid biological specimen separation device 10 has at least a closed configuration and an open configuration.

In a closed configuration, fasteners 38 are wrapped around pegs 48 and fastening tabs 50, thereby securing base 12 to cap 32. Contained in between base 12 and cap 32 is collection membrane 14, which is disposed in the second recess 46, and separation membrane 16, which is disposed in the first recess 44. Fasteners 38 urge cap 32 towards base 12 with sufficient force such that cap 32 collapses pores in separation membrane 16, thereby forming a liquid impermeable barrier 52 in between two regions of separation membrane 16. The liquid impermeable barrier 52 is dimensioned to be slightly larger in width (e.g. radius) than collection membrane 14, thereby minimizing the volume of plasma lost to lateral leakage and/or absorption by separation membrane 16.

In an open configuration, fasteners 38 are not wrapped around pegs 48 and fastening tabs 50, thereby allowing disassembly of the liquid biological specimen separation device 10. For example, collection membrane 14 and separation membrane 16 are removable from liquid biological specimen separation device 10 for use in various analytic techniques.

Sample deposition aperture 28 can have a diameter/width of 8.3 to 9.2 mm. That is, sample deposition aperture 28 can have a diameter/width of 8.3, 8.4, 8.5, 8.6, 8.7, 8.8, 8.9, 9.0, 9.1, or 9.2 mm.

Collection membrane 14 can have a diameter/width of 3 to 10.5 mm and a thickness of 0.19 mm to 0.270 mm.

First recess 44 can have a diameter/width of 10 to 25 mm.

Separation membrane 16 can have a diameter/width of 9 to 11 mm and a thickness of 0.19 mm to 0.380 mm.

Second recess 46 can have a diameter/width that is 0.1 to 0.5 mm larger than a diameter/width of collection membrane 14, and preferably has a diameter/width that is smaller than the sample deposition aperture 28.

Liquid impermeable barrier 52 can have a diameter/width that is 0.6 to 1.0 mm larger than a diameter of sample deposition aperture 28.

FIGS. 11A-11F show a liquid biological specimen separation device 10 in accordance with another embodiment of the invention. The liquid biological specimen separation device 10 of FIGS. 11A-11F is substantially the same as the liquid biological specimen separation device 10 of FIGS. 10A-10B except that base 12 is secured to cap 32 by a twist-lock mechanism 54 rather than fasteners 38, pegs 48, and fastening tabs 50. Base 12 and cap 32 each have complementary fastening protrusions 56 with ridge features 58. The complementary fastening protrusions 56 of base 12 and cap 32 can be engaged to secure base 12 to cap 32 and disengaged to unsecure base 12 from cap 32, respectively, by rotating base 12 relative to cap 32. When the complementary fastening protrusions 56 of base 12 and cap 32 are engaged with one another, cap 32 is urged towards base 12 with sufficient force such that cap 32 collapses pores in separation membrane 16, thereby forming a liquid impermeable barrier 52 in between two regions of separation membrane 16.

In operation, to secure cap 32 to base 12, complementary fastening protrusions 56 on cap 32 can be inserted into apertures 60 in base 12 that are dimensioned to receive complementary fastening protrusions 56. Cap 32 is then rotated relative to base 12 such that complementary fastening protrusions 56 and ridge features 58 on both base 12 and cap 32 are aligned and engaged. The reverse operations can be performed to unsecure cap 32 from base 12.

I. Applications and Use

Methods of using a liquid biological specimen separation device are provided. Generally, a liquid biological specimen separation device is used to receive a liquid biological specimen containing an analyte of interest, separate the liquid biological specimen into two components, and store an analyte of interest. The liquid biological specimen separation device is suitable for use as a point-of-care device.

In certain embodiments, the methods include providing a liquid biological specimen separation device and dispensing a liquid biological specimen onto a separation membrane of the device via an aperture in a cover and/or a cap. The liquid biological specimen flows through the separation membrane (e.g. via capillary action, gravity, etc). A first component of the liquid biological specimen is trapped/retained by the separation membrane while a second component of the liquid biological specimen flows through the separation membrane and into the collection membrane, which absorbs the second component. The second component can be dried in the collection membrane, either actively (e.g. via a desiccant or heating) or passively (e.g. air dry), before further processing. Alternatively, the second component can be used for further processing prior to being dried out (e.g. while still wet). The separation membrane and/or the collection membrane having the first and second components respectively can be removed from the device and be exposed to or placed in a reconstitution media to remove/recover analytes of interest therefrom, which can then be analyzed using a suitable technique for the analyte to be studied. In certain embodiments, the methods can include compressing the collection and/or separation membranes to aid in recovering analytes of interest therefrom. In certain embodiments, the methods can include applying reconstitution media to the separation and/or collection membranes to rehydrate analytes of interest contained therein, and compressing the membranes to release the analytes of interest. In certain embodiments, the separation devices and methods separate a liquid biological specimen into at least two constituent components that are subsequently air-dried and stored at ambient temperatures (e.g. without the need for refrigeration or freezing) prior to subsequent quantitative and qualitative analysis on at least one analyte of interest in at least one of the components.

In certain embodiments, the methods include providing a liquid biological specimen separation device. The methods can include adding approximately 20, 30, 40, 50, 60, 70, 80, 90, 100, 110, 120, 130, 140, 150, 160, 170, 180, 190, or 200 uL of whole blood from either a pipette or directly from a patient's finger-stick or heel-stick onto a top surface of a separation membrane of the device via an aperture in a cover and/or a cap. In embodiments, disposing 20-200 uL of whole blood onto a top surface of a separation membrane of the device results in 5-50 uL of plasma saturating a collection membrane. In embodiments, the volume of plasma is equal to about one-quarter the volume of whole blood. The methods can include adding approximately 25-40 uL of whole blood from either a pipette or directly from a patient's finger-stick or heel-stick onto a top surface of a separation membrane of the device via an aperture in a cover and/or a cap. In embodiments, disposing 25-40 uL of whole blood onto a top surface of a separation membrane of the device results in 6-10 uL of plasma saturating a collection membrane.

The methods can include having a user wait approximately 1, 2, 3, 4, 5, or 10 or more minutes for transfer of plasma through the separation membrane to the collection membrane (e.g. via capillary action, gravity, etc). The methods can include having a user allow the collection membrane to dry (e.g. placing the collection membrane in a designated air drying location) for 1, 2, 3, 4, 5, 6, 12, 24, or more hours. The drying can be accomplished at room temperature by air drying or at controlled temperature. The methods can include placing the whole device or the dried collection membrane in a sealable packaging, which can include a desiccant, for shipment to a laboratory for further analysis. The methods can include the laboratory separating the collection membrane from the separation device. The methods can include the laboratory separating white blood solids from the collection membrane. The methods can include the laboratory suspending the collection membrane in a reconstitution medium.

In certain embodiments, the reconstitution medium is molecular-grade water. In other embodiments, the reconstitution medium includes nuclease-free water or the components of phosphate buffered saline (PBS) or other suitable buffered saline solutions. Optionally, the reconstitution medium includes sodium azide or other antimicrobial agents. The reconstitution medium can also include any number or combinations of available biological preservatives or blood anticoagulants including but not limited to ethylenediaminetetraacetic acid (EDTA), sodium citrate, and heparin. Saline solutions or nuclease-free water can serve as a sterile and neutral medium for the rehydration, re-suspension, and recovery of analyte(s) of interest from the collection and/or separation membranes. When included, antimicrobial agents such as sodium azide prevent microbial growth and subsequent contamination with RNases. When included, biological preservatives such as EDTA, sodium citrate, and heparin serve as anticoagulants and or chelating agents.

The volume of a membrane may or may not expand upon absorption of a liquid biological specimen, and may or may not contract upon drying. However, a liquid saturated membrane can be compressed to release entrained fluid containing an analyte of interest, due to its porosity, by at least about 10%, 20%, 30%, 40%, 50%, 60%, 70%, 75%, 80%, 90%, or more of its saturated volume. Volumetric compression is one convenient technique for releasing analytes of interest, however, other means such as centrifugation or vacuum pressure can alternatively be employed to release analytes of interest from a membrane.

In certain embodiments, the methods can also include an intermediate step of applying a stabilizing composition to the collection membrane and/or the separation membrane to protect analytes of interest against degradation. Depending upon the analytes of interest, the stabilizing composition may include one or more of a weak base, a chelating agent, a protein denaturing agent such as a detergent or surfactant, a nuclease inhibitor, and a free radical trap. Particularly for protection of unstable RNA, the stabilizing composition may include RNase inhibitors and inactivators, genetic probes, complementary DNA or RNA (or functionally equivalent compounds), proteins and organic moieties that stabilize RNA or prevent its degradation.

In embodiments, the time periods for which analytes of interest may be preserved or stored on a collection and/or separation membrane can be for a period of several minutes, hours, days, months, or even greater.

Temperature conditions under which analytes of interest may be preserved or stored on a collection and/or separation membrane are not limited. Typically, analytes of interest are kept at ambient or room temperature, for example, from about 15° C. to about 40° C., preferably from about 15° C. to about 25° C. In some embodiments, the analytes of interest may be kept in a cool environment. For example, in short-term storage, the analytes can be refrigerated at about 2° C. to about 10° C. In yet another example, the analytes may be refrigerated at about 4° C. to about 8° C. In another example, in long-term storage, the analytes can be frozen at about −20° C. to about −80° C. In addition, the membranes may preferably, but not necessarily, be stored in dry or desiccated conditions or under an inert atmosphere.

In certain embodiments, whole blood is dispensed onto a liquid biological specimen separation device. In such embodiments, whole blood or a liquid suspension thereof is deposited onto a separation membrane. The separation membrane absorbs the whole blood. The separation membrane captures some solid components of whole blood (e.g., WBCs, RBCs, platelets, and/or other cellular components) while allowing fluidic and/or other solid whole blood components (e.g. cell-free plasma) to pass through the separation membrane via gravity and/or capillary action. The components of whole blood passing through the separation membrane are absorbed by the collection membrane.

In certain embodiments, cell-free plasma captured on the collection membrane can be removed/recovered from the collection membrane by exposing the collection membrane to a reconstitution media. The recovered cell-free plasma can contain an analyte of interest, for instance, nucleic acids such as DNA and RNA, which can be used for viral load quantitation, genotyping, drug resistance testing, or other suitable analyses. The analytes of interest can be detected or analyzed using analytical and diagnostic methods known in the art.

The detailed description set forth above is provided to aid those skilled in the art in practicing the invention. However, the invention described and claimed herein is not to be limited in scope by the specific embodiments described above, as these embodiments are presented as mere illustrations of several aspects of the invention. Any combinations and modifications of the described methods and components, and compositions used in the practice of the methods, in addition to those not specifically described, will become apparent to those skilled in the art based on the present disclosure and do not depart from the spirit or scope of the present invention. Such variations, modifications, and combinations are also encompassed by the present disclosure and fall within the scope of the appended claims.

What is claimed is:

1. A liquid biological specimen separation device comprising:
    a base;
    a well raised away from the base;
    a collection membrane disposed on the well;
    a separation membrane disposed on the collection membrane;
    a cap disposed on the separation membrane and removably complementary mated with the well in a closed configuration, wherein the cap comprises an aperture therein configured to allow deposition of a liquid biological specimen therethrough; and
    at least two elastomeric band fasteners,
    wherein the cap removably adheres to the base by the at least two elastomeric band fasteners,
    wherein the cap is removable from the well to change from the closed configuration into an open configuration, and wherein the collection membrane and the separation membrane are secured between the cap and the well in the closed configuration.

2. The device of claim 1, wherein the separation membrane has a porosity that gradually decreases from a first side to a second side so as to filter and trap solid components of a liquid biological specimen deposited on the separation membrane.

3. The device of claim 1, wherein the separation membrane is configured to filter and trap solid components of a biological specimen, the biological specimen being selected from the group consisting of whole blood, plasma, urine, saliva, sputum, semen, vaginal lavages, bone marrow and cerebrospinal fluid.

4. The device of claim 1, wherein the separation membrane is configured to filter and trap solid components of a whole blood specimen, and wherein the collection membrane is configured to separately filter and trap a plasma fraction or filtrate of the whole blood specimen.

5. The device of claim 1, wherein the separation membrane has a pore size ranging from 0.1-20 μm.

6. The device of claim 1, wherein the separation membrane comprises a polysulfone polymer material selected from the group consisting of asymmetric sub-micron polysulfone and asymmetric super micron polysulfone.

7. The device of claim 1, wherein the collection membrane comprises a substantially hydrophobic polyolefin material comprising a plurality of polypropylene fibers coated with hydrophobic polyethylene.

8. The device of claim 1, wherein the collection membrane, the separation membrane, or both, comprise microglass fibers.

9. The device of claim 1, wherein the cap removably adheres to the base.

10. The device of claim 1, wherein the cap is urged towards the base.

11. The device of claim 10, wherein the separation membrane comprises a liquid impermeable barrier between two regions of the separation membrane formed from collapsed pores in the separation membrane as a result of the urging.

12. The device of claim 1, further comprising an identifier disposed on the base.

13. The device of claim 1, wherein the well comprises a first recess and a second recess.

14. The device of claim 13, wherein the first recess and second recess are dimensioned to receive the separation membrane and the collection membrane, respectively.

15. The device of claim 13, wherein the second recess is disposed in the first recess.

16. The device of claim 1, wherein the aperture, the separation membrane, and the collection membrane are aligned about an axis extending through a center point of each of the aperture, the separation membrane, and the collection membrane in the closed configuration.

17. A method for separating plasma from whole blood comprising:
providing a device according to claim 1; and
depositing whole blood through the aperture and onto the separation membrane.

18. The method of claim 17, wherein 25-40 uL of whole blood is deposited onto the separation membrane.

19. The method of claim 17, wherein 6-10 uL of plasma are recovered in the collection membrane.

* * * * *